(12) United States Patent
Traidia et al.

(10) Patent No.: US 11,624,743 B2
(45) Date of Patent: Apr. 11, 2023

(54) APPARATUS AND METHOD FOR THE NON-DESTRUCTIVE MEASUREMENT OF HYDROGEN DIFFUSIVITY

(71) Applicant: Saudi Arabian Oil Company, Dhahran (SA)

(72) Inventors: Abderrazak Traidia, Abqaiq (SA); Mohammed Alshahrani, Jeddah (SA); Sebastien A. Duval, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 450 days.

(21) Appl. No.: 16/805,126

(22) Filed: Feb. 28, 2020

(65) Prior Publication Data
US 2020/0200727 A1    Jun. 25, 2020

Related U.S. Application Data

(63) Continuation of application No. 15/530,697, filed on Apr. 28, 2017, now Pat. No. 10,732,163.

(51) Int. Cl.
*G01N 33/00* (2006.01)
*G01N 33/2025* (2019.01)
(Continued)

(52) U.S. Cl.
CPC ......... *G01N 33/2025* (2019.01); *G01N 13/00* (2013.01); *G01N 27/413* (2013.01);
(Continued)

(58) Field of Classification Search
CPC .................................................. G01N 33/2025
(Continued)

(56) References Cited

U.S. PATENT DOCUMENTS

| | | | |
|---|---|---|---|
| 3,731,523 A | 5/1973 | Vissers et al. | |
| 4,065,373 A | 12/1977 | Martin et al. | |

(Continued)

FOREIGN PATENT DOCUMENTS

| | | |
|---|---|---|
| CN | 101832966 A | 9/2010 |
| EP | 1238247 A2 | 9/2002 |
| GB | 2490395 A | 10/2012 |

OTHER PUBLICATIONS

Kim et al, "Determination of Hydrogen Diffusion Parameters of Ferritic Steel from Electrochemical Permeation Measurement under Tensile Loads" In Journal of the Electrochemical Society, 161 (12) (2014).

(Continued)

*Primary Examiner* — Christine T Mui
*Assistant Examiner* — Emily R. Berkeley
(74) *Attorney, Agent, or Firm* — Leason Ellis LLP

(57) ABSTRACT

Apparatuses and methods of measuring a hydrogen diffusivity of a metal structure including during operation of the metal structure, are provided. A hydrogen charging surface is provided at a first location on an external surface of the structure. In addition, a hydrogen oxidation surface is provided at a second location adjacent to the first location on the external surface of the structure. Hydrogen flux is generated and directed into the metal surface at the charging surface. At least a portion of the hydrogen flux generated by the charging surface is diverted back toward the surface. A transient of the diverted hydrogen fluxes measured, and this measurement is used to determine the hydrogen diffusivity of the metal structure in service.

4 Claims, 20 Drawing Sheets

(51) Int. Cl.
  G01N 27/413 (2006.01)
  G01N 13/00 (2006.01)
  G01N 1/22 (2006.01)
  C01B 3/00 (2006.01)
  H01M 4/94 (2006.01)
  C25B 1/02 (2006.01)
  H01M 4/92 (2006.01)
  G01N 33/20 (2019.01)

(52) U.S. Cl.
  CPC ............ *C01B 3/001* (2013.01); *C25B 1/02* (2013.01); *G01N 33/20* (2013.01); *G01N 2001/2241* (2013.01); *G01N 2013/003* (2013.01); *H01M 4/92* (2013.01); *H01M 4/94* (2013.01)

(58) Field of Classification Search
  USPC .......................................................... 436/87
  See application file for complete search history.

(56) References Cited

U.S. PATENT DOCUMENTS

| | | |
  |---|---|---|
  | 4,221,651 A | 9/1980 | Mansfeld et al. |
  | 4,563,249 A | 1/1986 | Hale |
  | 5,279,169 A | 1/1994 | Freeman |
  | 5,405,513 A | 4/1995 | Lewis, II et al. |
  | 6,196,060 B1 | 3/2001 | Yepez et al. |
  | 6,554,981 B2 * | 4/2003 | Lewis, II ............ G01N 27/4045 204/404 |
  | 6,637,253 B2 | 10/2003 | Dean et al. |
  | 7,306,951 B1 | 12/2007 | Benson et al. |
  | 7,552,643 B2 | 6/2009 | Aikens |
  | 2005/0238932 A1 | 10/2005 | Koyama et al. |
  | 2015/0301010 A1 | 10/2015 | Valentini |

OTHER PUBLICATIONS

Mohtadi Bonb M A et al., "Hydrogen induced cracking susceptibility in different layers of a hot rolled X70 pipeline steel," International Journal of Hydrogen Energy, vol. 38, No. 31, p. 13831-13841. Oct. 17, 2013.

International Search Report and Written Opinion from corresponding International Application No. PCT/US2018/029298, dated Jul. 3, 2018. 91 pages.

Office Action in counterpart Chinese Application No. 201880027468.6, dated Aug. 3, 2021, 37 pages.

Ouyang yue-jun et al., Field monitoring test of hydrogen permeation sensor, Modern Chemical Industry, vol. 35, No. 10, pp. 167-170, Oct. 31, 2015.

Zhong Zhen-qian et al.; Effect of strip inclusion on hydrogen diffusion in 0Cr16Ni5Mo steel, Transactions of Materials and Heat Treatment, vol. 37, No. 2, pp. 84-89, Feb. 28, 2016.

* cited by examiner

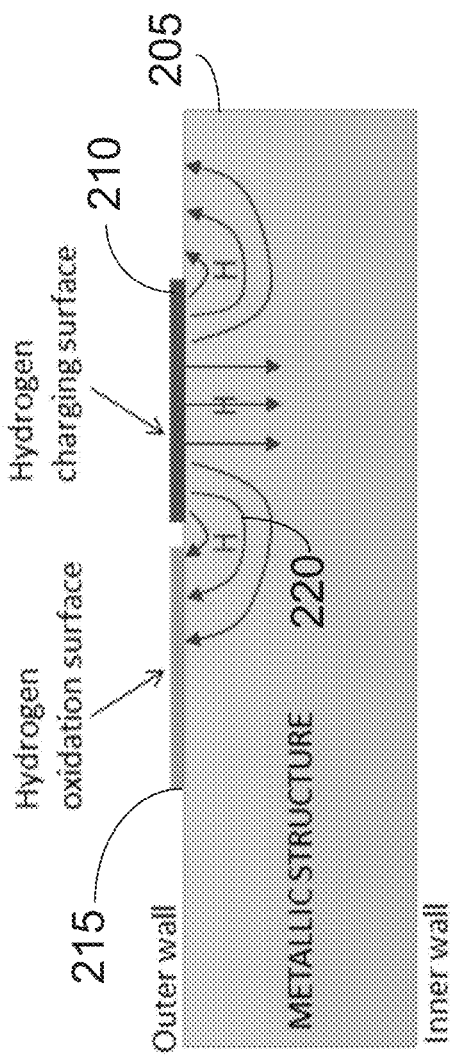
FIG. 2A
FIG. 2B
FIG. 2C

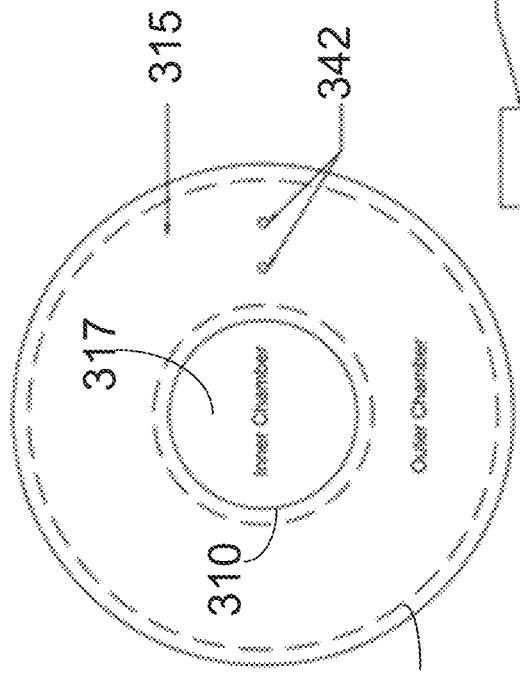
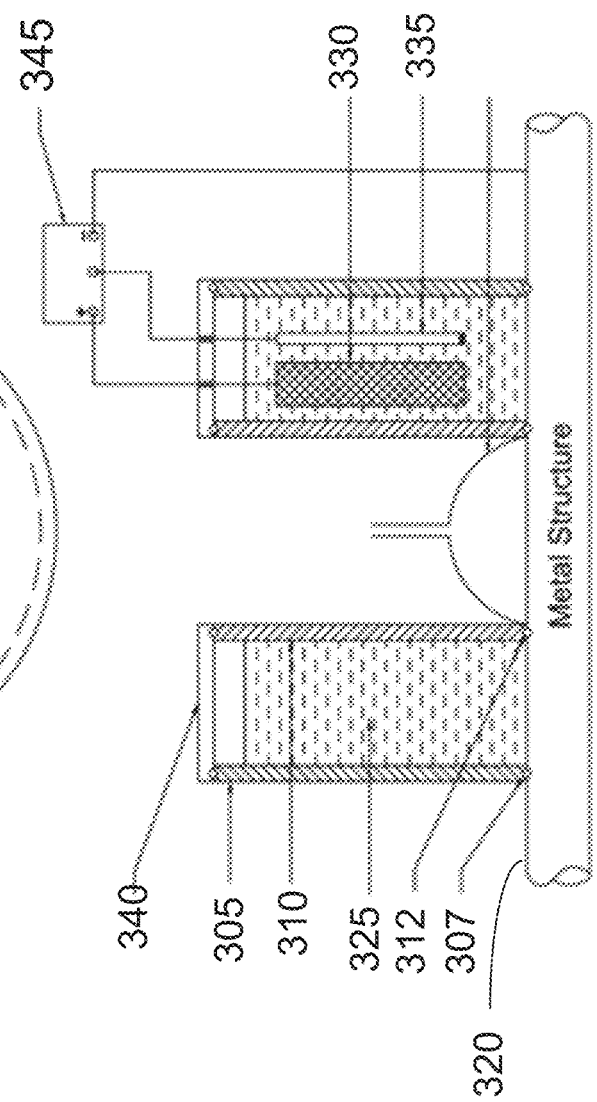
FIG. 3A
FIG. 3B

APPARATUS AND METHOD FOR THE NON-DESTRUCTIVE MEASUREMENT OF HYDROGEN DIFFUSIVITY

CROSS-REFERENCE TO PRIOR APPLICATION

This application is a continuation of, and claims priority from, U.S. patent application Ser. No. 15/530,697, titled APPARATUS AND METHOD FOR THE NON-DESTRUCTIVE MEASUREMENT OF HYDROGEN DIFFUSIVITY, filed Apr. 28, 2017, which is hereby incorporated by reference in its entirety.

FIELD OF THE INVENTION

The present invention relates to material inspection and in particular relates to apparatuses and methods for non-destructive measurement of hydrogen diffusivity.

BACKGROUND OF THE INVENTION

Hydrogen embrittlement is a phenomenon in which mechanical properties of metallic materials, such as tensile strength and ductility, deteriorate due to the uptake of hydrogen. Such degradations decrease the fracture resistance of metals such as steel.

The hydrogen atom ranks as the smallest in diameter among the elements. Hydrogen atoms are easily adsorbed on metal surfaces from which they diffuse into the interior by jumping between the interstitial lattices of tetrahedral/octahedral sites. Hydrogen can be also trapped at metallurgical defects and imperfections in steel such as grain boundaries, dislocations, inclusions etc. Once atomic hydrogen is absorbed, it may precipitate at high-stress zones such as defects, inclusions, voids or discontinuities where a recombination reaction can take a place. The recombination can cause embrittlement, leading eventually to cracking. As hydrogen accumulates, linkage of such high-stress zones allows cracks to propagate through the metal.

Hydrogen diffusivity ($D_H$) is a property of the metal determines the rate at which hydrogen travels in the material and plays a major role in hydrogen damage development. Hydrogen damage such as hydrogen-induced cracking is likely to grow faster in high diffusivity materials due to an increased pressure build-up rate. Therefore, accurate knowledge of $D_H$ for a specific material of interest is a crucial input to hydrogen damage evolution models and lifetime prediction tools.

The review of the related art shows that there is a significant discrepancy between published values of $D_H$ even for the same steel grade (see table 1). For example, for X65 pipeline steel, reported values of diffusivities range from $10^{-5}$ cm²/s to $10^{-7}$ cm²/s, which is a variation of two orders of magnitude. The large discrepancies can be explained by multiple factors such as the difference in steel microstructure, specimen thickness, surface preparation and permeation test conditions.

TABLE 1

| STEEL TYPE | EXPERIMENTAL METHOD | HYDROGEN DIFFUSIVITY at 25 C. (cm2/s) |
|---|---|---|
| X65 | Permeation | $9.49 \times 10^{-7}$ |
| X52 | | |
| X70 | Permeation | $0.1\text{-}0.9 \times 10^{-7}$ |
| | | $0.1\text{-}0.3 \times 10^{-7}$ |
| X100 | Permeation | $1.04 \times 10^{-8}$ |

TABLE 1-continued

| STEEL TYPE | EXPERIMENTAL METHOD | HYDROGEN DIFFUSIVITY at 25 C. (cm2/s) |
|---|---|---|
| X80 | Permeation | $5.32 \times 10^{-9}$ |
| X70 | Permeation | $2.63 \times 10^{-7}$ |
| X65 | Permeation | $1.5 \times 10^{-6}$ |
| X120 | Permeation | $2.0\text{-}2.8 \times 10^{-7}$ |
| X65 | Permeation | $0.8\text{-}2.7 \times 10^{-9}$ |
| X-52 | Permeation | $7 \times 10^{-7}$ to $3.2 \times 10^{-5}$ |
| X-60 | Permeation | $5.6\text{-}11.5 \times 10^{-7}$ |
| X-65 | | $0.9\text{-}4.6 \times 10^{-7}$ |
| X-80 | | $4.7 \times 10^{-7}$ |
| X-100 | | $3.9 \times 10^{-7}$ |
| X-65 | | $4.2 \times 10^{-7}$ |
| X-85 | | $4.0 \times 10^{-7}$ |
| X-60 | Permeation | $3.5 \times 10^{-6}$ |

Due to this large variability in measured $D_H$ values, it is important that $D_H$ be measured directly on a portion of the metallic structure of interest to ensure accuracy. The directly measured value of $D_H$ can then be used as an input to a prediction model. The main challenge for such direct measurement is that the standard measurement technique, as described in ISO 17081, is destructive in nature, as it requires extracting and machining a test specimen from the equipment of interest. Obtaining a test specimen in this manner is usually impossible for installed and operational metallic structures.

The standard technique of ISO 17081 is based on the use of the electrochemical cell of Devanathan and Stachurski, shown in FIG. 1A. An electrochemical cell 100 includes a charging cell 110 and an oxidation cell 120. The charging cell 110 includes a platinum auxiliary (counter) electrode 114 and a calomel reference electrode 118. Similarly, the oxidation cell 120 includes a platinum auxiliary (counter) electrode 124 and a calomel reference electrode 128. A sample 130 is placed between the charging cell 110 and the oxidation cell 120. In operation, the charging cell 110 induces generation of hydrogen on the side of the sample surface 130 exposed to the charging cell. Some of the hydrogen generated on the charging cell side diffuses through the sample to the oxidation cell 120, where the hydrogen atoms are oxidized. The oxidation process is facilitated by keeping the sample 130 at a positive potential of around (+300 mV) against the standard calomel electrode 118. The use of palladium coating at the exit side can enhance the oxidation process further. The oxidized hydrogen is measured at an outlet port as a function of the oxidized current density. From the curve of oxidation current over time, $D_H$ is typically calculated using the time lag method.

The time lag method is appropriate for determining $D_H$ over a single dimension, e.g., the diffusivity of hydrogen from one side of a specimen to the other. It is derived from the one-dimensional diffusion equation. The analytical solution for the transient permeation flux is provided in ISO-17081 as:

$$\frac{J_{perm}(t)}{J_{SS}} = 1 + \sum_{n=1}^{\infty}(-1)^n \exp(-n^2\pi^2\tau) \quad (1)$$

where $J_{perm}(t)$ is the transient permeation flux, $J_{SS}$ is the steady state permeation flux (i.e, $J_{SS}=J_{perm}(t=\infty)$) and $\tau$ is the normalized time expressed as function of the diffusion coefficient and the specimen thickness L as follows:

$$\tau = \frac{D_H}{tL^2} \quad (2)$$

A plot of the normalized permeation flux $$\left(\frac{J_{perm}}{J_{SS}}\right)$$

versus normalized time τ is illustrated in FIG. 1B (with a log scale on the time axis). The usefulness of this curve (hereafter referred to as the 'standard master curve') is that it is independent of the hydrogen charging concentration $C_0$, the specimen thickness L, and the hydrogen diffusivity $D_H$. In other words, for any hydrogen permeation experiment that satisfies the one-dimensional conditions shown in FIG. 1A, a plot of $$\left(\frac{J_{perm}}{J_{SS}}\right)$$

vs. τ will stick to this standard master curve. Tabulated values of this curve are provided in the ISO standard 17081, such that if the specimen thickness L and the permeation transient $J_{perm}(t)$ are known, the hydrogen diffusivity $D_H$ can be easily determined from any point on the curve. In practice, the point on the curve where $$\frac{J_{perm}}{J_\infty} = 0.63$$

is commonly used. This point corresponds to a normalized time $\tau = \tau_{lag} = 1/6$. The physical time corresponding to $\tau_{lag}$ is noted $t_{lag}$ and is therefore by definition equal to $$t_{lag} = \frac{6L^2}{DH}.$$

From the latter the hydrogen diffusivity $D_H$ is easily derived as:

$$DH = \frac{L^2}{6t_{lag}} \quad (3)$$

The standard technique discussed above requires a test specimen and access to both sides of the specimen. As noted, this technique is not applicable to determining hydrogen diffusivity of metal structures in the field or to multi-dimensional hydrogen permeation flux. There is therefore a need for a non-destructive measurement technique able to carry out on-site and in-service measurement of hydrogen diffusivity as required. The embodiments of the present invention address this need.

SUMMARY OF THE INVENTION

According to one aspect of the present invention, a method of measuring a hydrogen diffusivity of a metal structure is provided. A hydrogen charging surface is provided at a first location on an external surface of the structure. In addition, a hydrogen oxidation surface is provided at a second location adjacent to the first location on the external surface of the structure. Hydrogen flux is generated and directed into the metal surface at the charging surface. A portion of the hydrogen flux is diverted from the metal surface toward the oxidation surface at which a current representative of a transient of the hydrogen flux is detected. The transient of the hydrogen flux used to determine the hydrogen diffusivity of the metal structure. The hydrogen charging surface is produced by a first electrochemical cell and the hydrogen oxidation surface is produced by a second electrochemical cell. In some implementations, the method further comprises measuring an oxidation current in the oxidation cell in order to measure the transient.

In some embodiments, a coating is added at the oxidation surface to promote oxidation of hydrogen. The coating can include deposited palladium or a palladium foil.

In some embodiments of the method of measuring hydrogen diffusivity, hydrogen diffusivity is determined from the transient of hydrogen flux using a direct simulation technique based on a Fickian diffusion model that uses initial conditions based on an experimental apparatus. Implementations of these embodiments include setting a value for the hydrogen diffusivity, executing the diffusion model using the set value of hydrogen diffusivity, comparing results of the Fickian diffusion model to results using the experimental apparatus, and repeating the previous steps with different values of hydrogen diffusivity until a closest match between the results of the diffusion model and the results using the experimental apparatus is reached.

In alternative embodiments of the method for measuring hydrogen diffusivity, hydrogen diffusivity is determined using a simulated master graph for a particular experimental apparatus design, the simulated master graph independent of geometric dimensions, and experimental parameters. Implementations of these embodiments include performing sensitivity analysis on each parameter to determine an influence of the parameter on a normalized transient permeation curve, and identifying the curve as a master curve, with respect to a parameter, if the curve is invariant to changes in the parameter. The parameters can include hydrogen charging concentration, hydrogen diffusivity of the metal structure, and general geometric parameters of the apparatus design such as metal structure thickness, a size of the charging surface, a width of the oxidation surface and a wall thickness of the charging cell.

According to another aspect of the present invention, an apparatus for measuring a hydrogen diffusivity of a metal structure is provided. The apparatus comprises a first chamber positioned on an external surface of the metal structure, the first chamber including a hydrogen charging cell that generates hydrogen at a hydrogen charging surface for diffusing into the external surface of the metal structure, and a second chamber separated by a wall from and adjacent to the first chamber and positioned on the external surface of the metal structure, the second chamber including an oxidation cell that generates an oxidation surface for receiving hydrogen flux diverted from the metals structure. A measurement of hydrogen diffusivity is derivable from a hydrogen oxidation current within the oxidation cell.

In some embodiments, the apparatus further comprises a palladium coating positioned at the oxidation surface for promoting oxidation of the permeated hydrogen.

According to embodiments of the apparatus of the present invention, the hydrogen charging cell includes a first electrolyte solution and the oxidation cell includes a second electrolyte solution, both the first and second electrolyte solutions being in contact with the external surface of the metal structure. In some implementations, a first counter electrode is positioned in the hydrogen charging cell, and a second counter electrode and a second reference electrode are positioned in the oxidation cell. A first electric power supply is coupled to the hydrogen charging cell and operative to provide a constant current, and a second electric power supply is coupled to the oxidation cell and operative to provide a constant voltage. The reference electrode located in the oxidation cell maintains a constant potential, and is used to gauge the quality of measurements taken.

Some embodiments of the apparatus may be implemented using an inner casing enclosing the hydrogen charging cell, and an outer casing enclosing the inner casing and the oxidation cell, the oxidation cell positioned between the inner casing and the outer casing. In further implementations, an alignment element positioned is between the inner casing and the outer casing to ensure that the inner chamber is concentric within the outer chamber.

In alternative embodiments, the apparatus may be implemented using an inner casing enclosing the oxidation cell, and an outer casing enclosing the inner casing and the hydrogen charging cell, the hydrogen charging cell positioned between the inner casing and the outer casing. In further implementations, an alignment element positioned is between the inner casing and the outer casing to ensure that the inner chamber is concentric within the outer chamber.

Further embodiments of the apparatus according to the present invention includes a first sealing element for preventing leakage of the first electrolyte solution, a second sealing element for preventing leakage of the second electrolyte solution. In some implementations, the sealing element comprises a magnet.

These and other aspects, features, and advantages can be appreciated from the following description of certain embodiments of the invention and the accompanying drawing figures and claims.

versus normalized time $\tau$ according to the prior art.

FIG. 2A is a schematic cross-sectional illustration of a wall of a metal structure permeated by a hydrogen flux according to the present invention via a charging surface and oxidation surface.

FIG. 2B shows an exemplary graph of a charging current over time applied at the charging surface of FIG. 2A.

FIG. 2C shows an exemplary graph of oxidation current over time measured for three different metallic materials.

FIG. 3A is a top cross-sectional view of an apparatus for measuring hydrogen diffusivity according to an exemplary embodiment of the present invention that employs a hydrogen flux sensor.

FIG. 3B a side cross-sectional view of the apparatus of FIG. 3A.

Figure 1A:
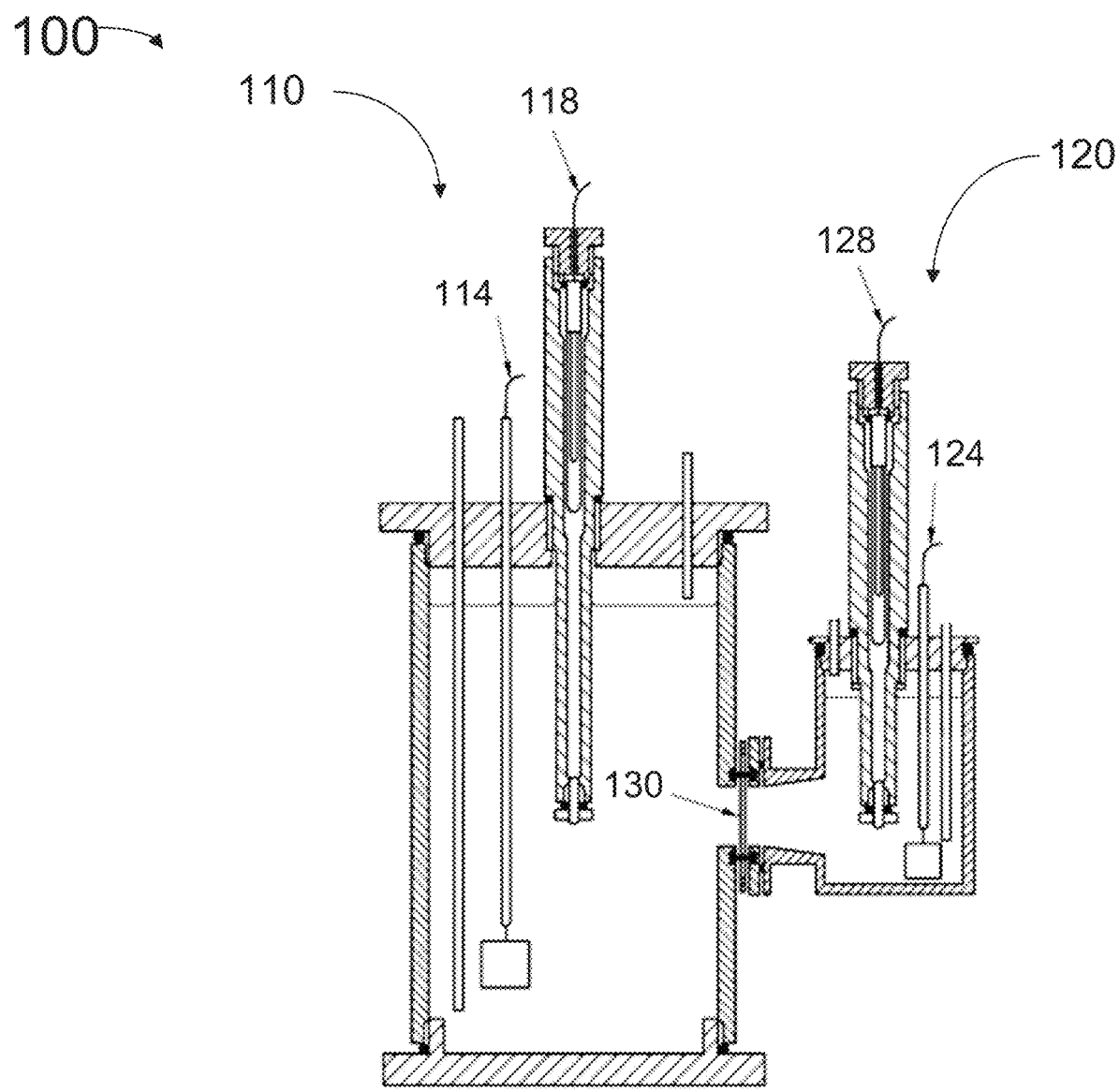
FIG. 1A is a front cross-sectional view of an apparatus for determining the hydrogen diffusivity of a metal material according to the prior art.
Figure 1B:
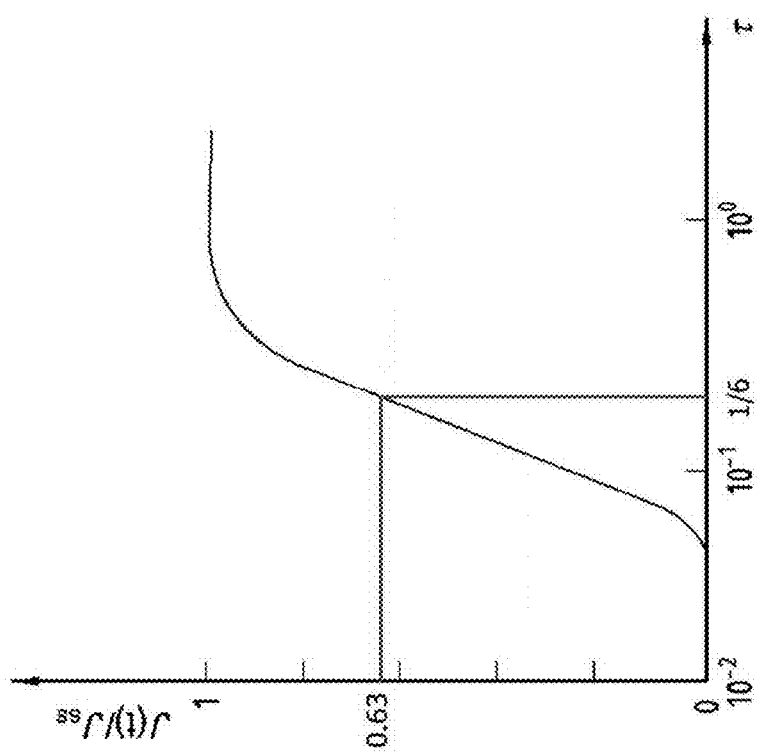
FIG. 1B is a graph of normalized permeation flux $$\left(\frac{J_{perm}}{J_{SS}}\right)$$
Figure 3C:
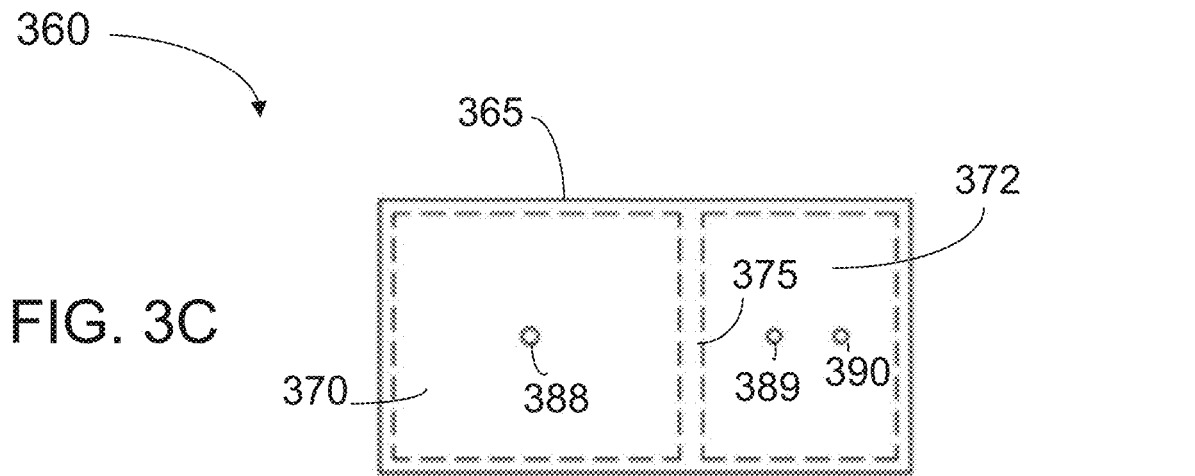

FIG. 3C is top cross-sectional view of another embodiment of an apparatus for measuring hydrogen diffusivity according to the present invention that employs a hydrogen flux sensor.

Figure 3D:
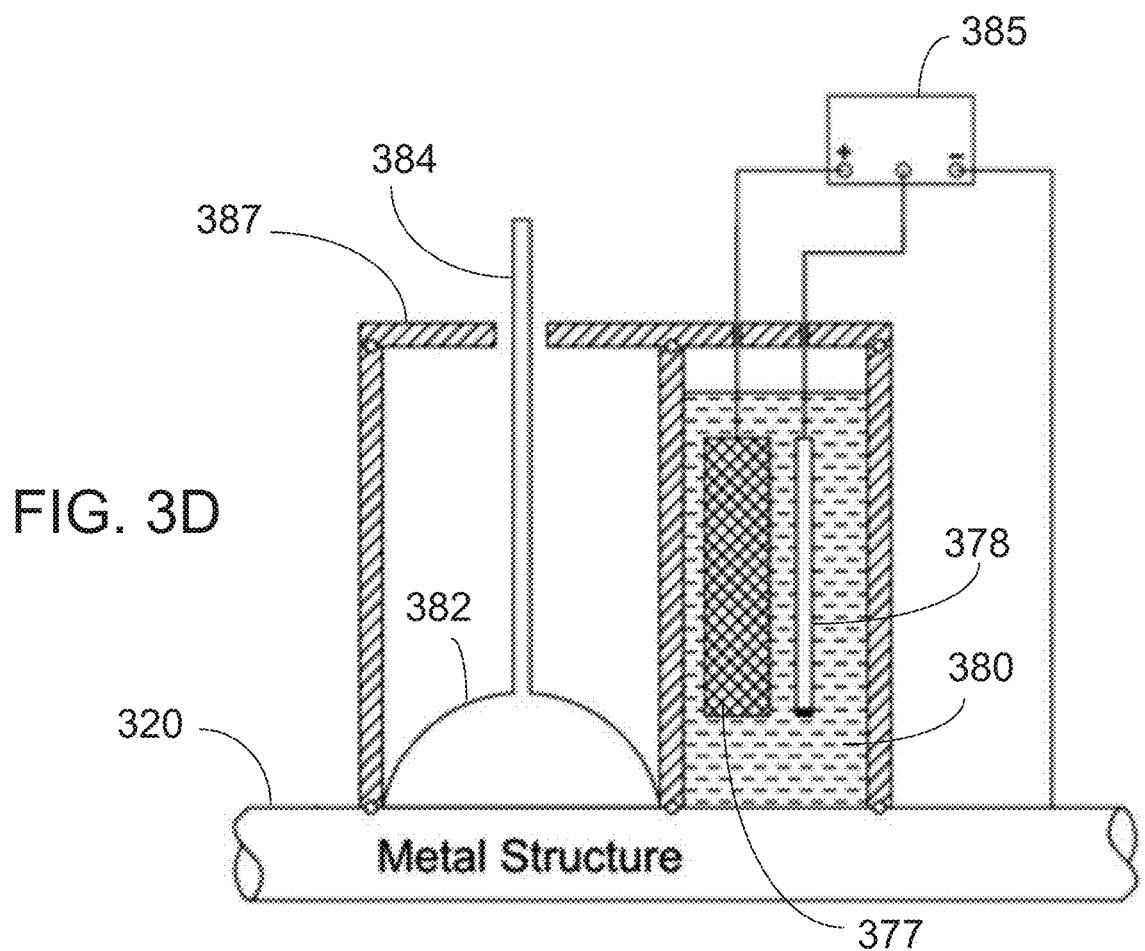

FIG. 3D is a side cross-sectional view of the apparatus of FIG. 3C.

Figure 3E:
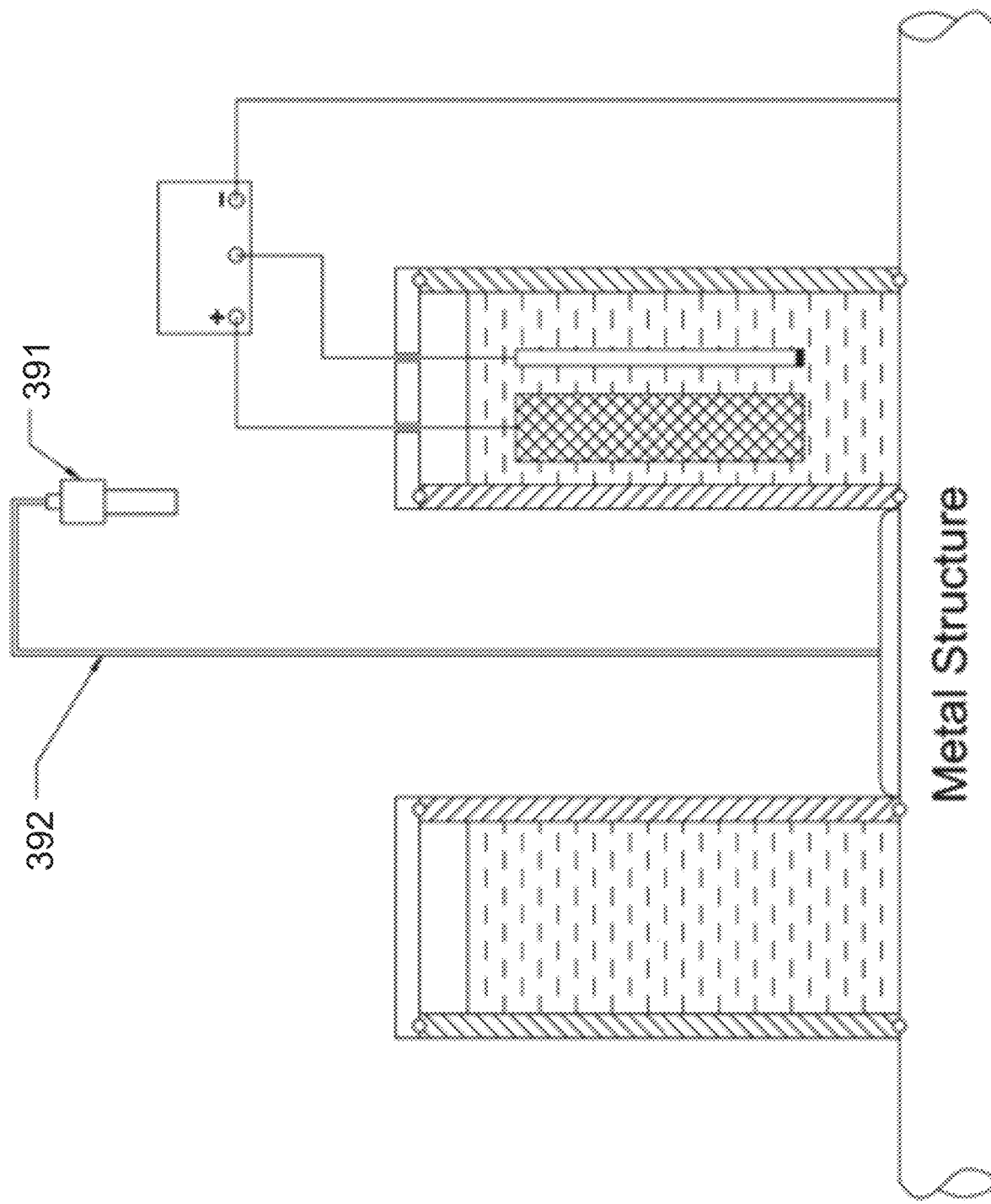

FIG. 3E is a cross-sectional view of the apparatus of FIG. 3B implemented with a commercial hydrogen flux sensor.

Figure 3F:
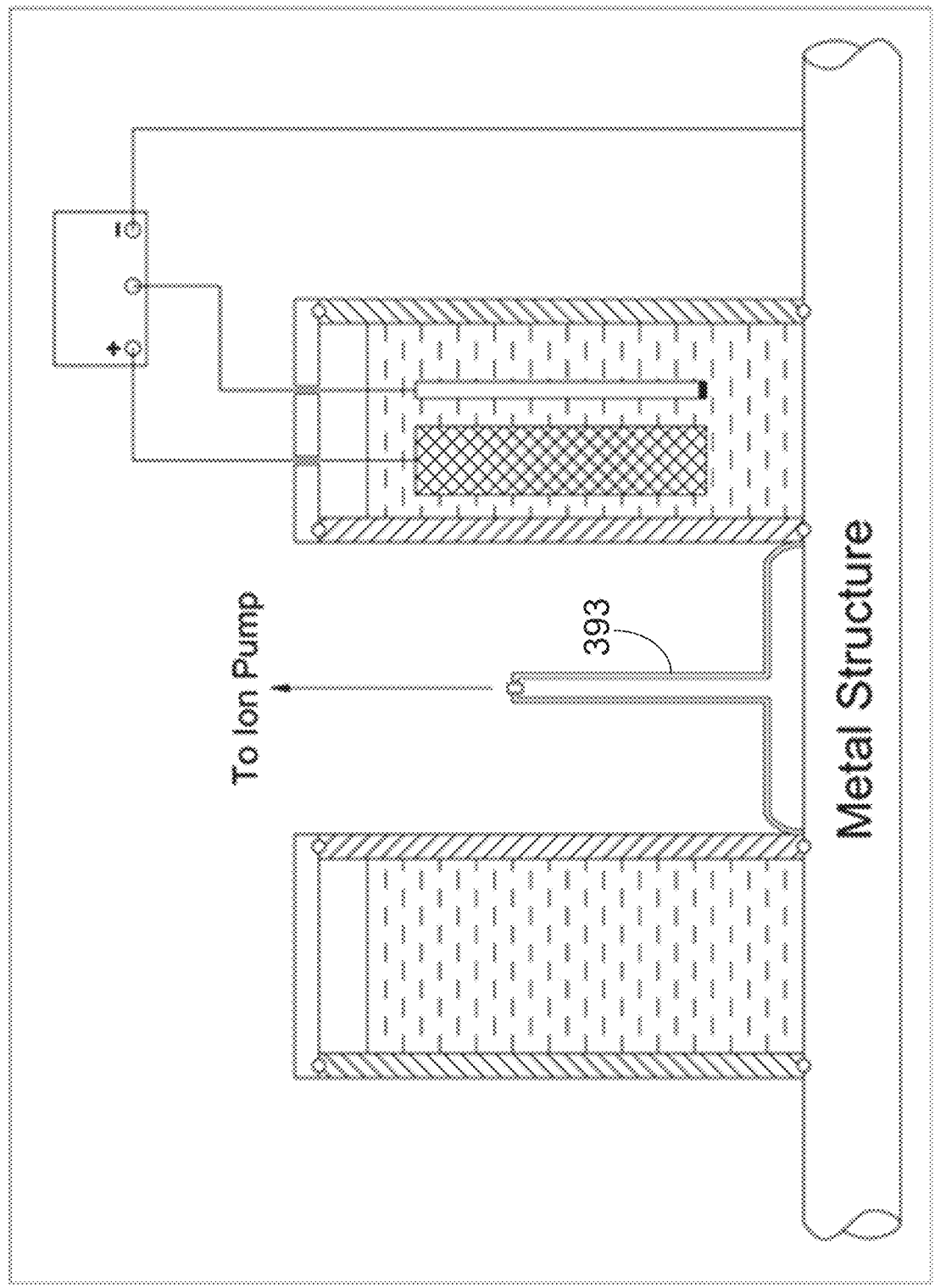

FIG. 3F is a cross-sectional view of the apparatus of FIG. 3B implemented with an ion pump for measuring hydrogen flux.

Figure 3G:
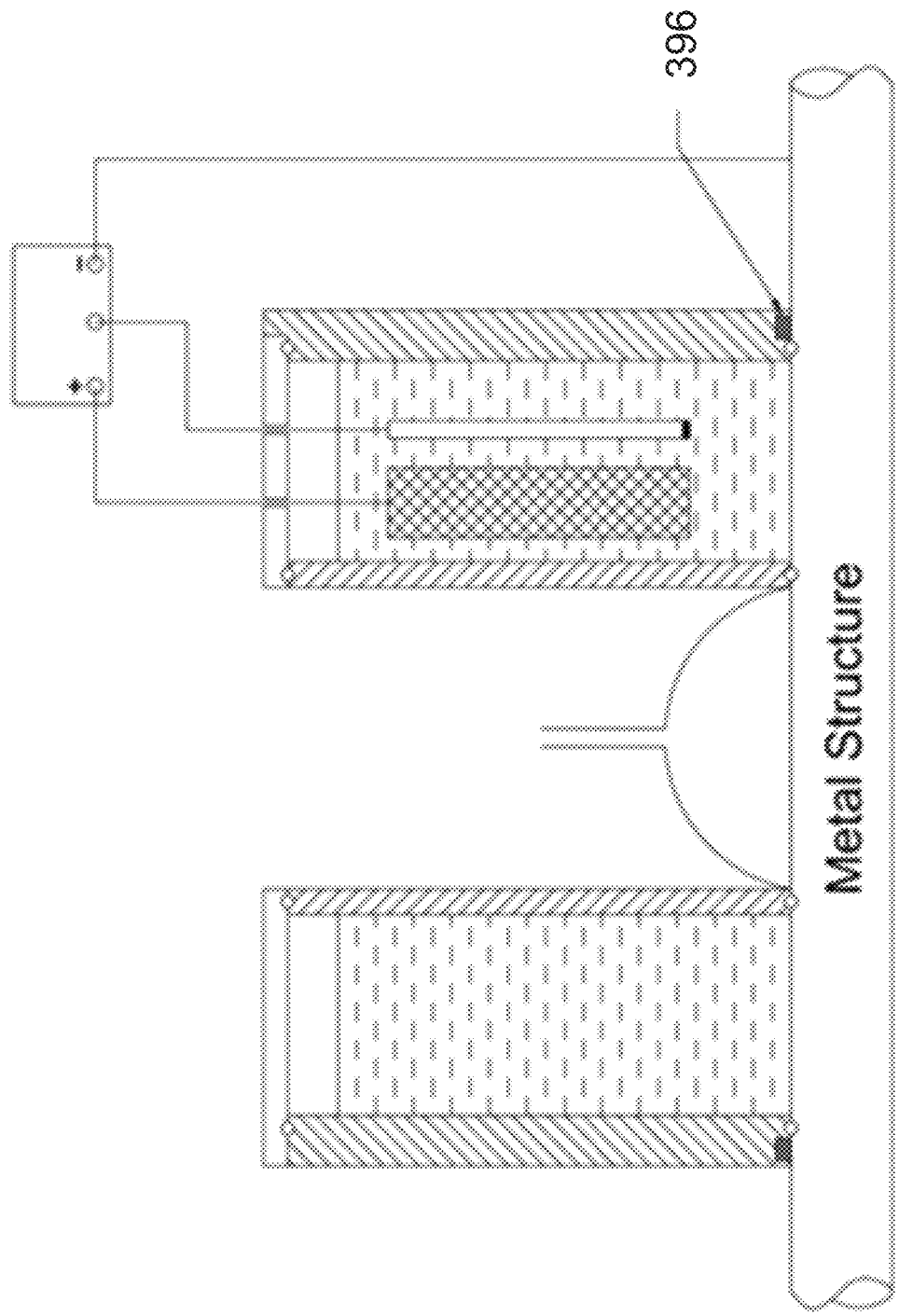

FIG. 3G is a side cross-sectional view of another embodiment of an apparatus for measuring hydrogen diffusivity according to the present invention that employs a hydrogen flux sensor.

Figure 3H:
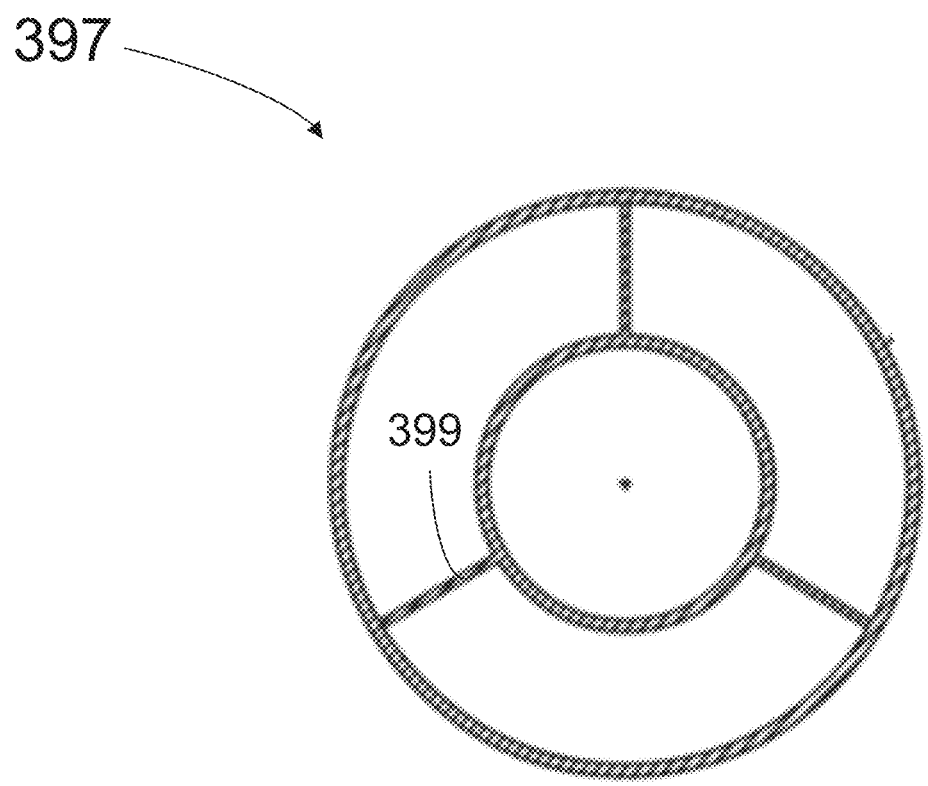

FIG. 3H is a top cross-sectional view of another embodiment of an apparatus for measuring hydrogen diffusivity according to the present invention that employs a hydrogen flux sensor.

Figure 3I:
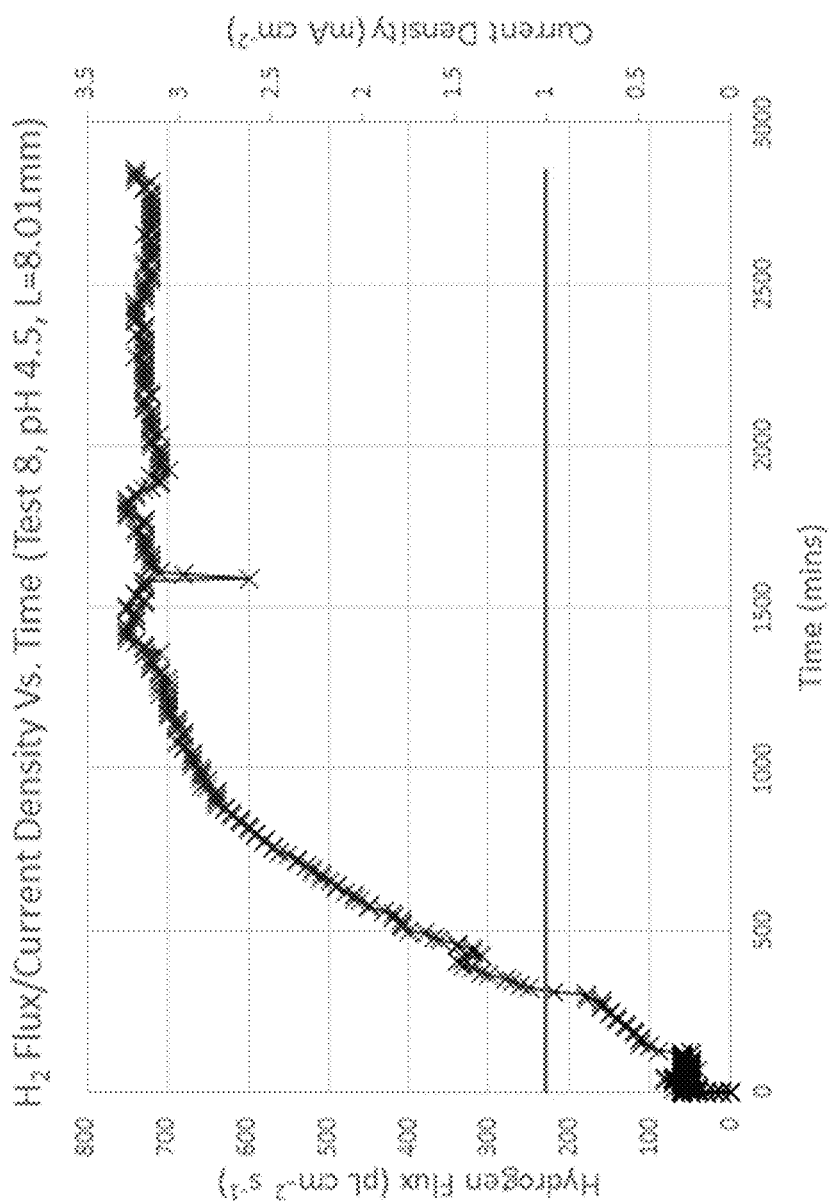

FIG. 3I is a graph showing experimental results of detected hydrogen flux over time using the apparatus of FIGS. 3A, 3B.

Figure 4A:
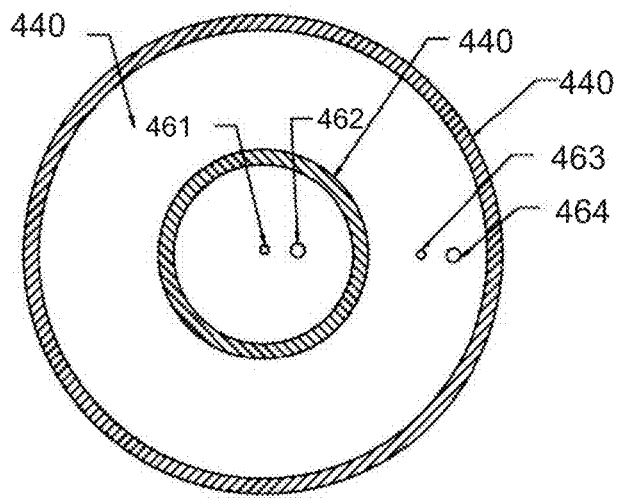

FIG. 4A is a top cross-sectional view of an apparatus for measuring hydrogen diffusivity according to an exemplary embodiment of the present invention that employs electrochemical cells for charging and oxidation.

Figure 4B:
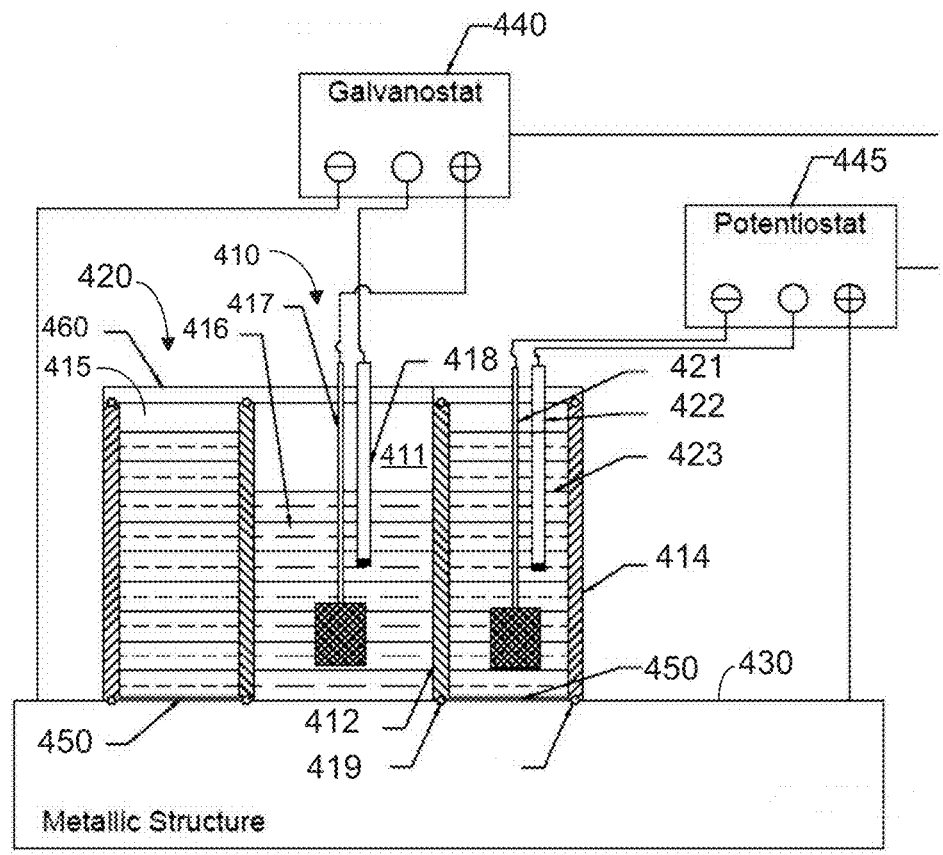

FIG. 4B a side cross-sectional view of the apparatus of FIG. 4A.

Figure 4C:
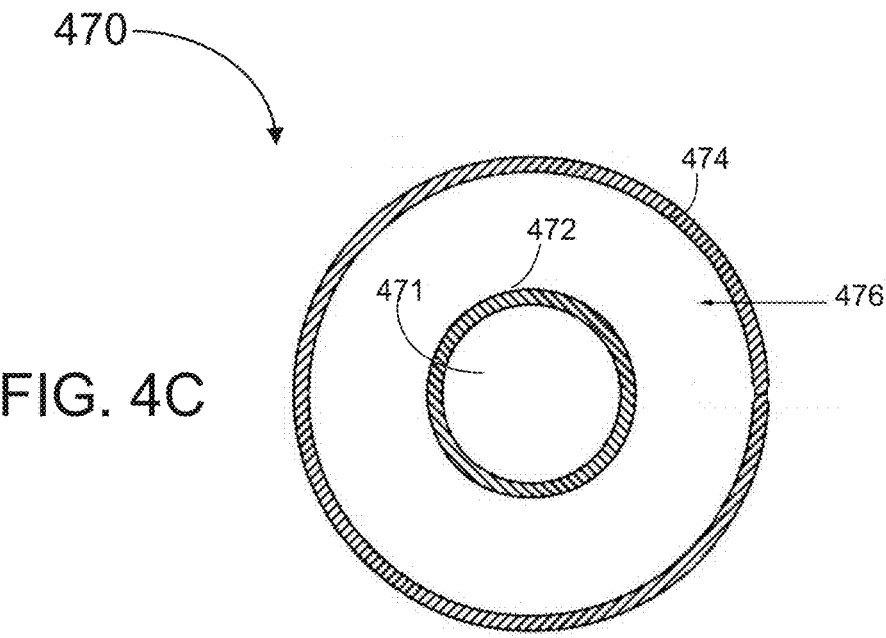

FIG. 4C is a top cross-sectional view of another embodiment of an apparatus for measuring hydrogen diffusivity according to the present invention that employs electrochemical cells for charging and oxidation.

Figure 4D:
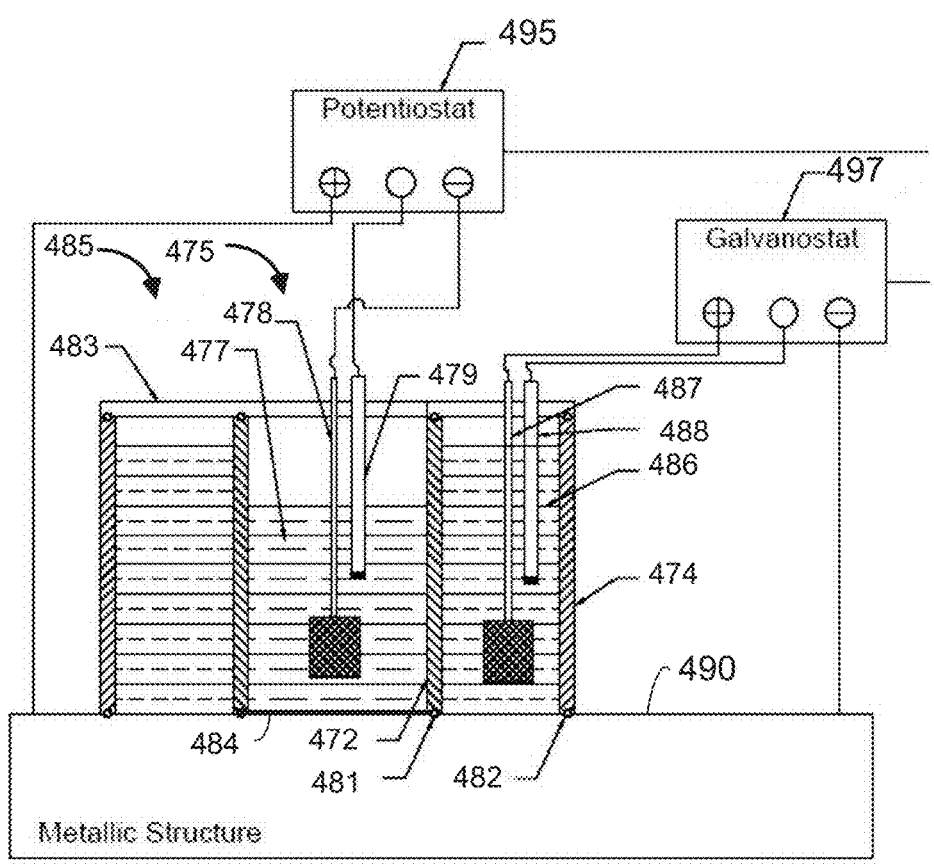

FIG. 4D is a side cross-sectional view of the apparatus of FIG. 4C.

Figure 4E:
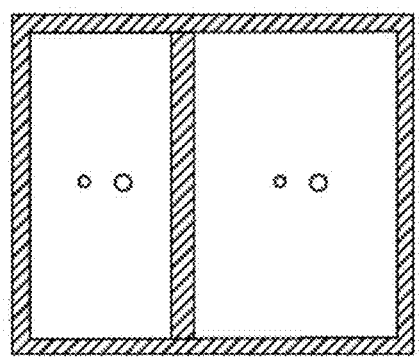

FIG. 4E is a top cross-sectional view of another embodiment of an apparatus for measuring hydrogen diffusivity according to the present invention that employs electrochemical cells for charging and oxidation.

Figure 4F:
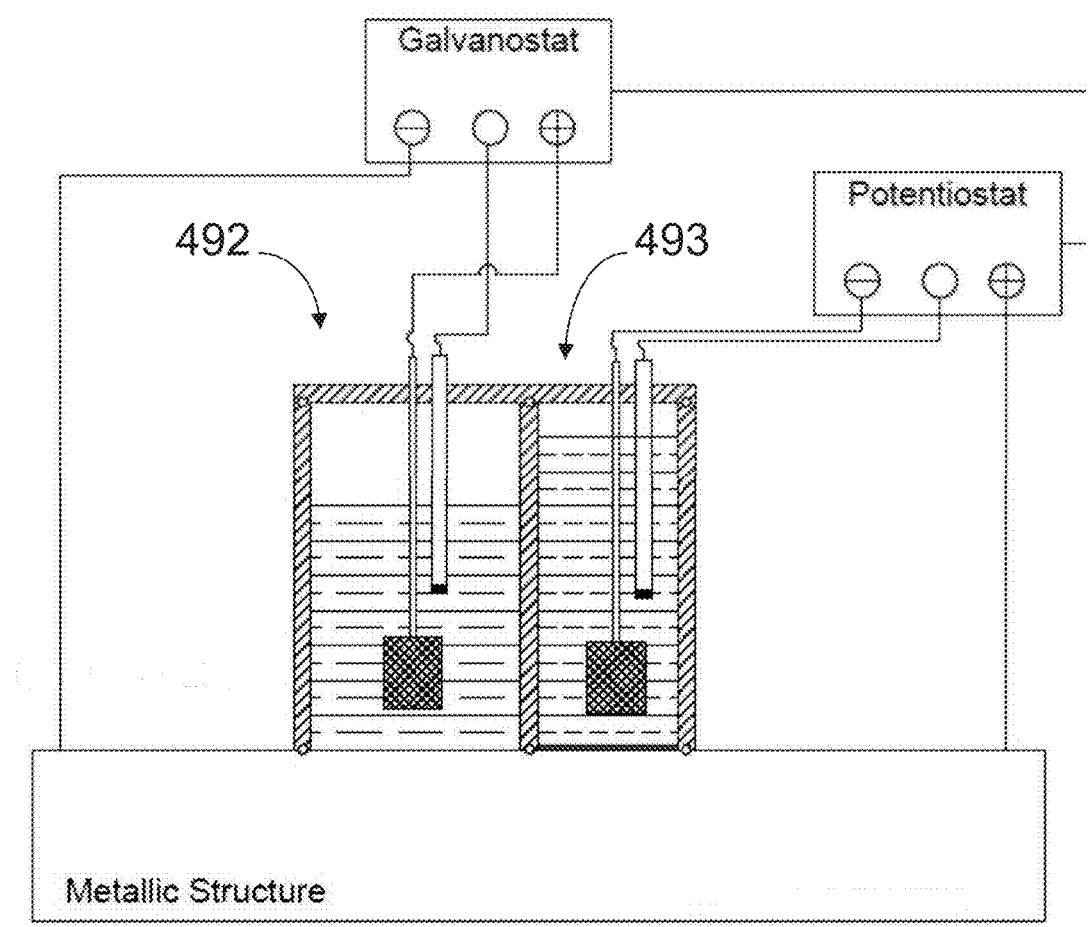

FIG. 4F is a side cross-sectional view of the apparatus of FIG. 4E.

Figure 4G:
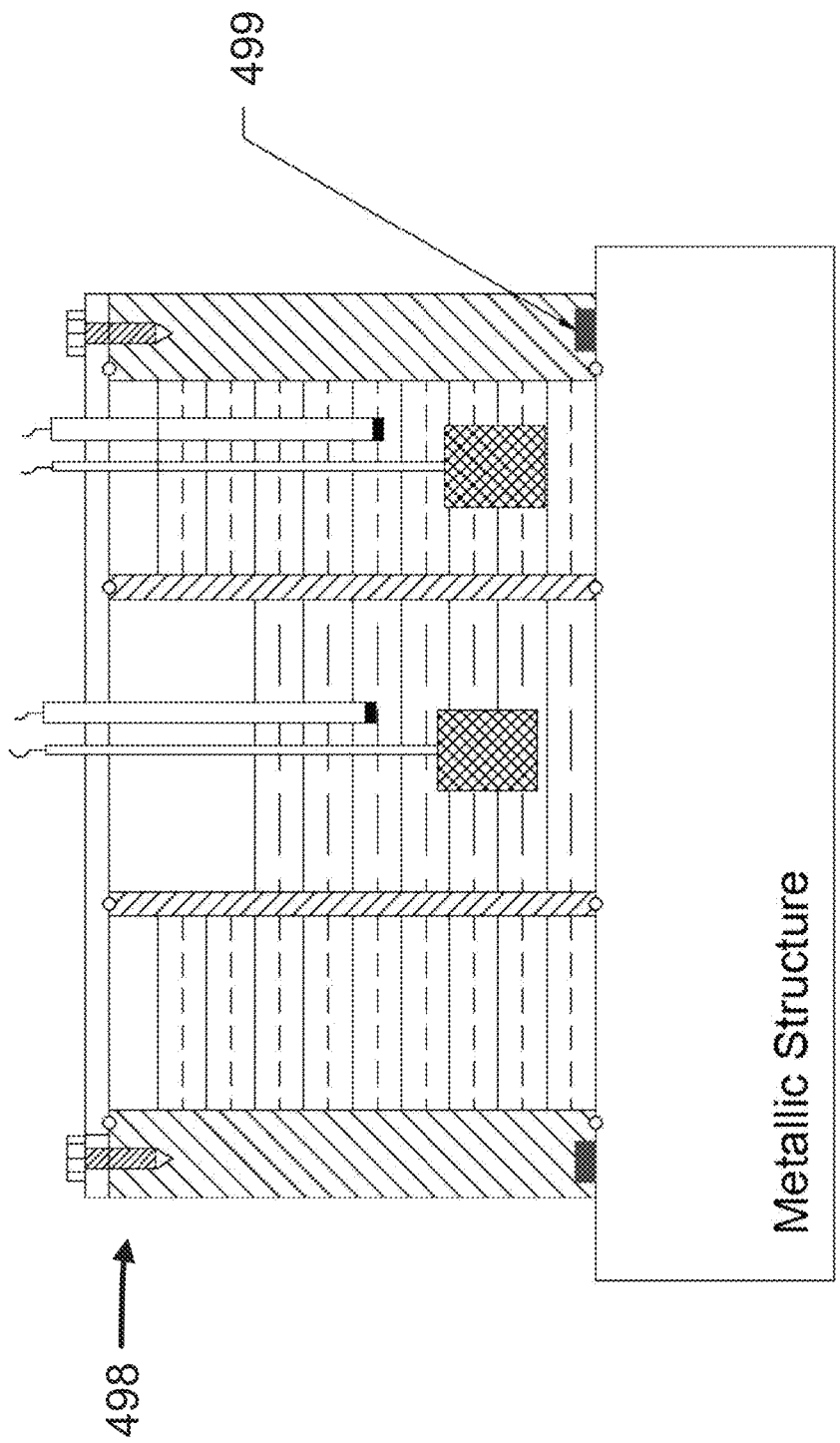

FIG. 4G is a side cross-sectional view of another embodiment of an apparatus for measuring hydrogen diffusivity according to the present invention that employs electrochemical cells for charging and oxidation.

Figure 5:
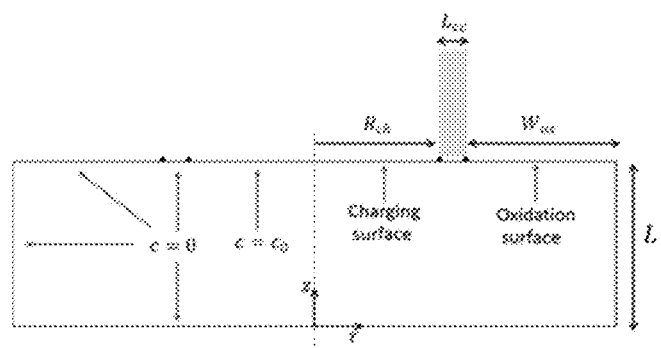

FIG. 5 is a schematic illustration of exemplary boundary conditions for a method of determining hydrogen diffusivity using the direct simulation technique according to an embodiment of the present invention.

Figure 6:
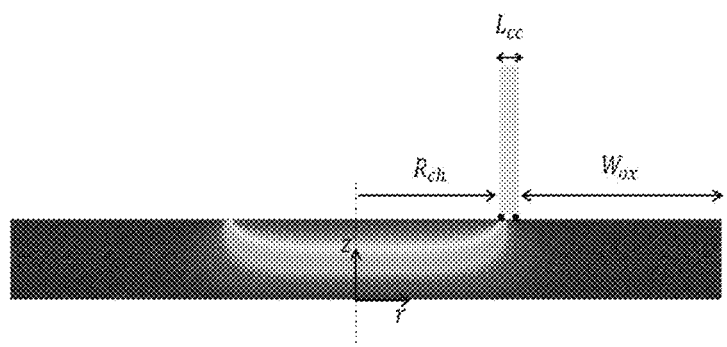

FIG. 6 shows an exemplary result of the direct simulation technique according to the present invention. A distribution of hydrogen concentration C and the streamlines of hydrogen flux throughout the specimen thickness are illustrated.

Figure 7A:
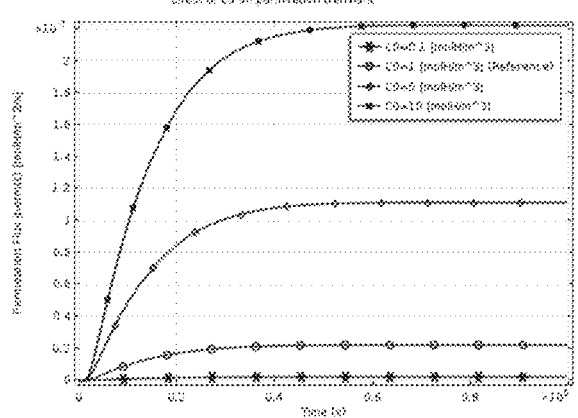
Figure 7B:
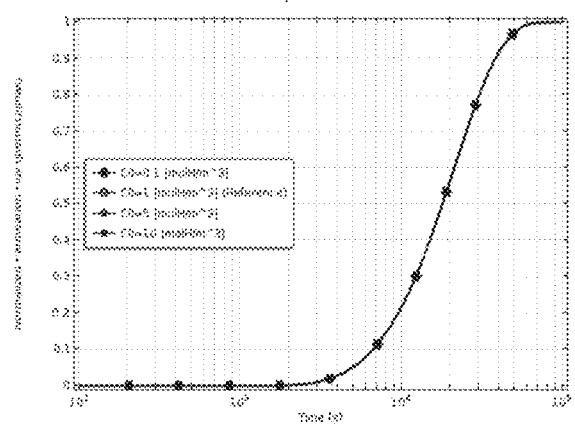

FIG. 7A is a graph of hydrogen flux (permeation) over time for several different values of $C_0$; FIG. 7B is a graph of the normalized hydrogen flux over time for the same values of $C_0$.

Figure 8:
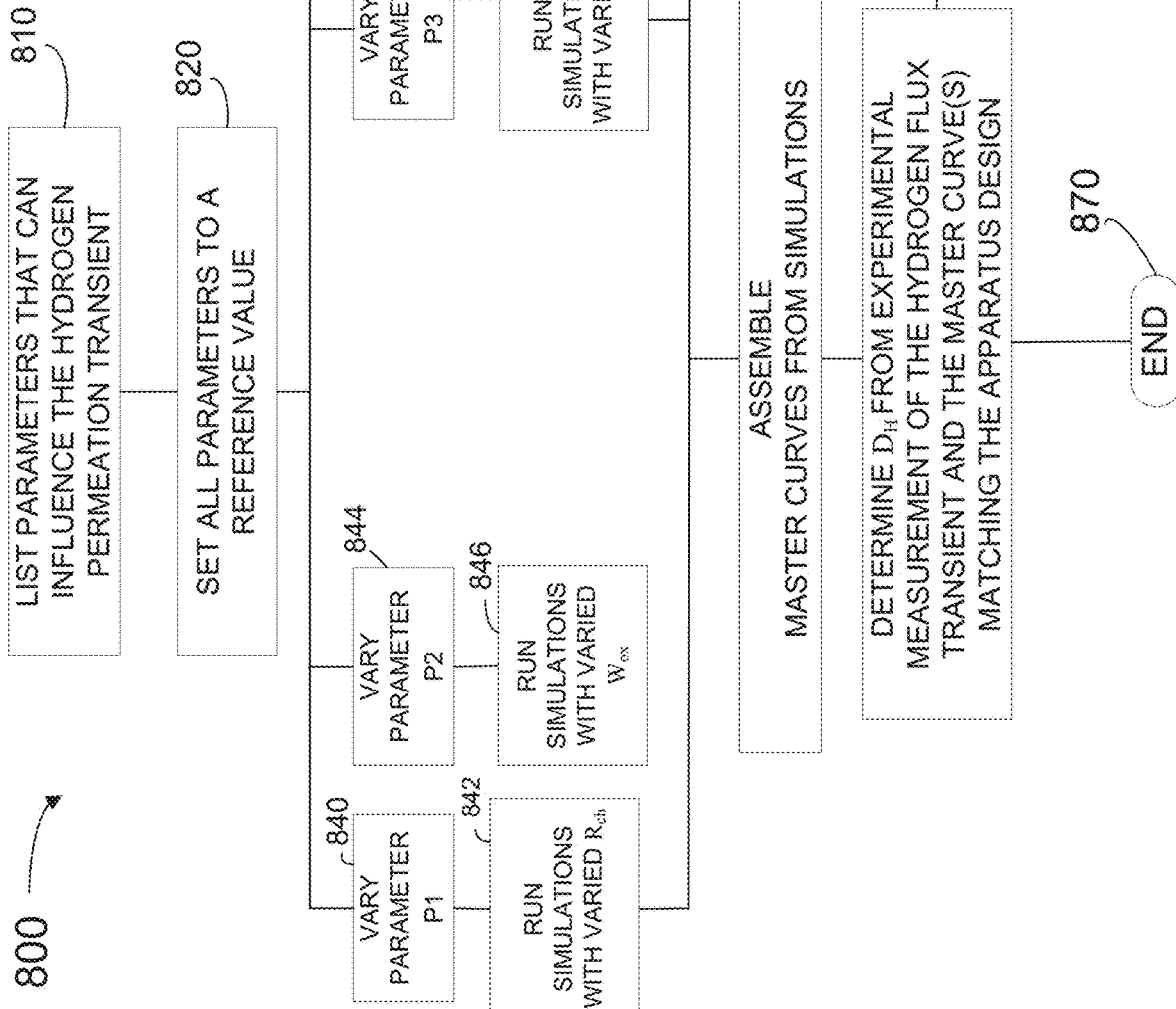

FIG. 8 is a flow chart of a method for determining hydrogen diffusivity using the standard master graphs simulation technique according to an embodiment of the present invention.

Figure 9:
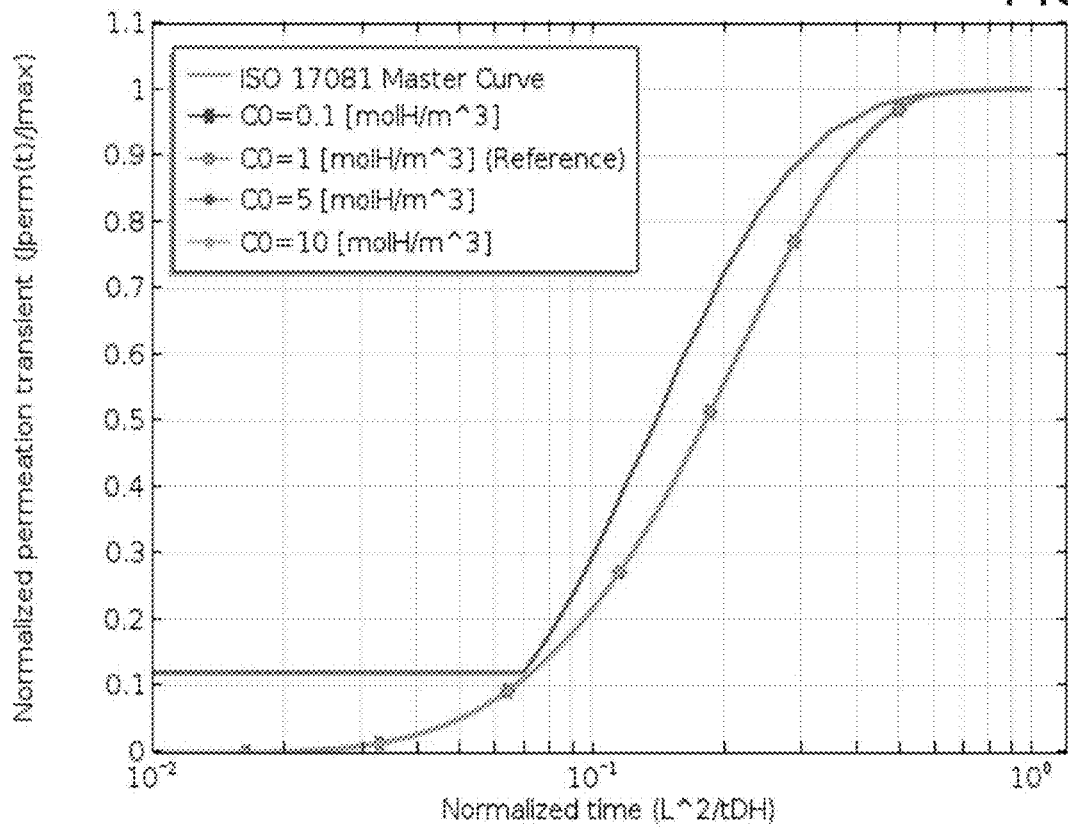

FIG. 9 shows results of a simulation of hydrogen flux for the apparatus of FIGS. 3A, 3B by varying the value $C_0$ and keeping other parameters constant according to the simulated master graphs technique of the present invention.

Figure 10:
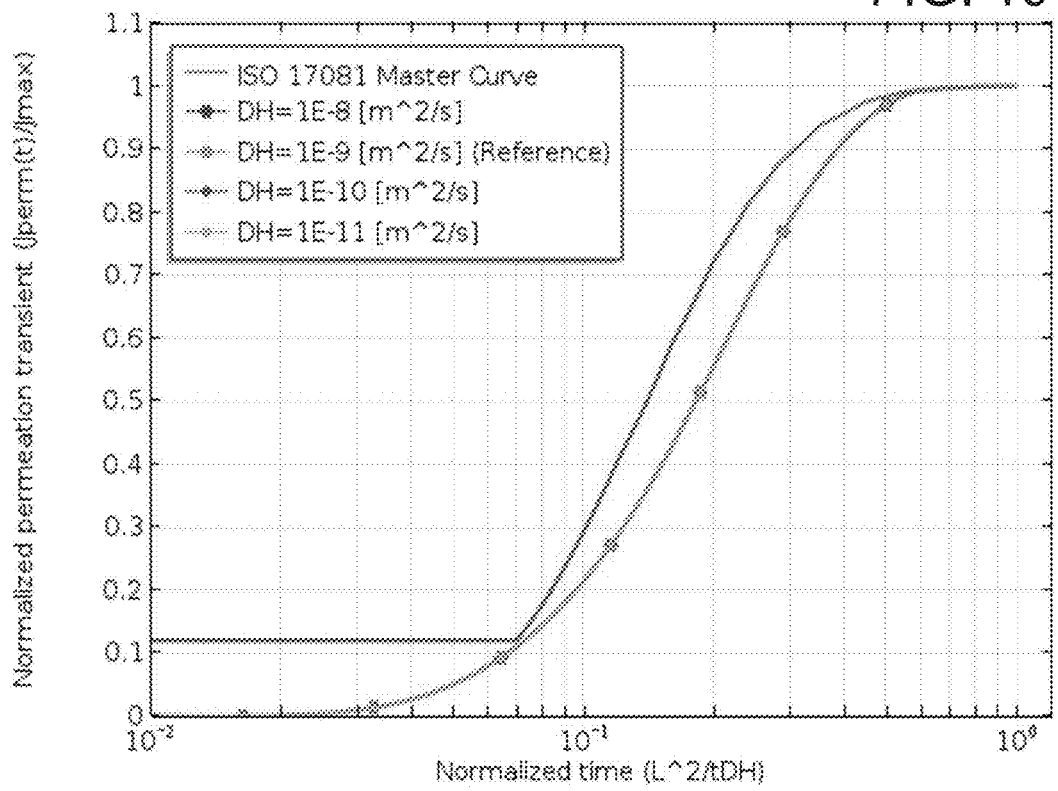

FIG. 10 shows results of a simulation of hydrogen flux for the apparatus of FIGS. 3A, 3B by varying the value $D_H$ and keeping other parameters constant according to the simulated master graphs technique of the present invention.

Figure 11:
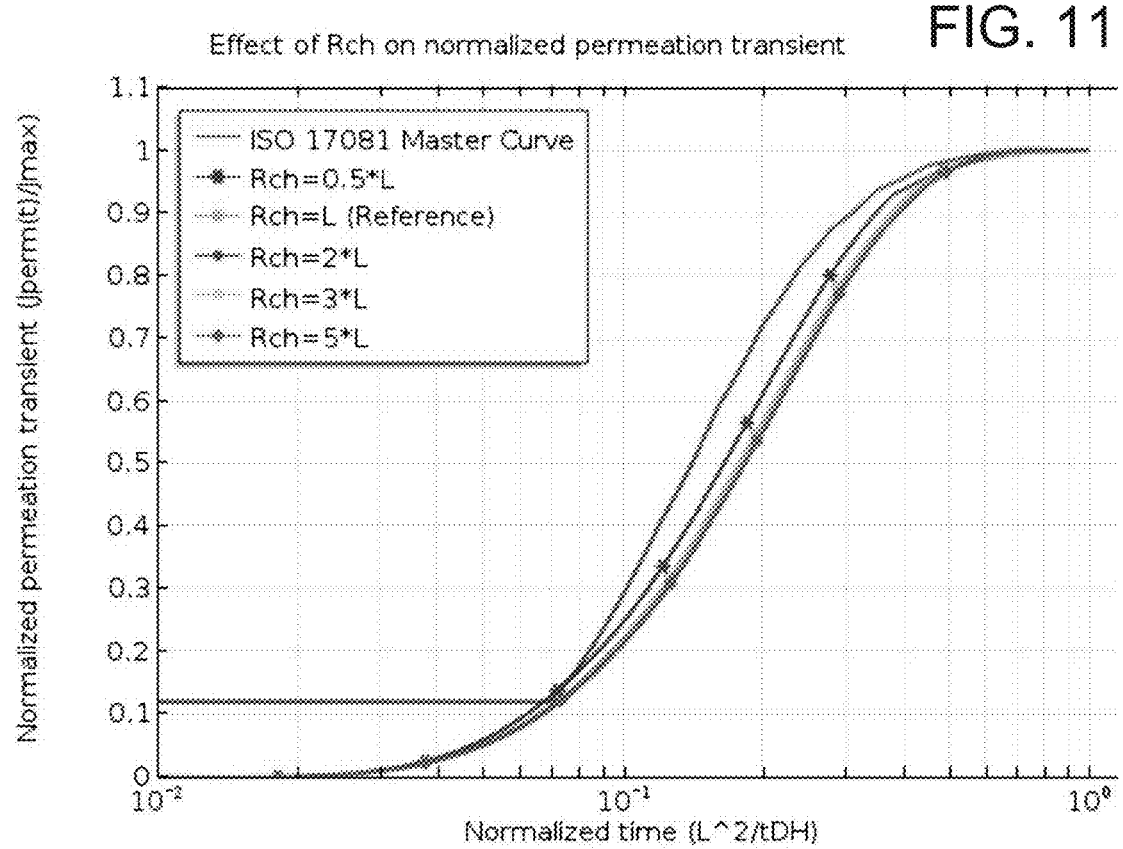

FIG. 11 shows results of a simulation of hydrogen flux for the apparatus of FIGS. 3A, 3B by varying the value $R_{ch}$ and keeping other parameters constant according to the simulated master graphs technique of the present invention.

Figure 12:
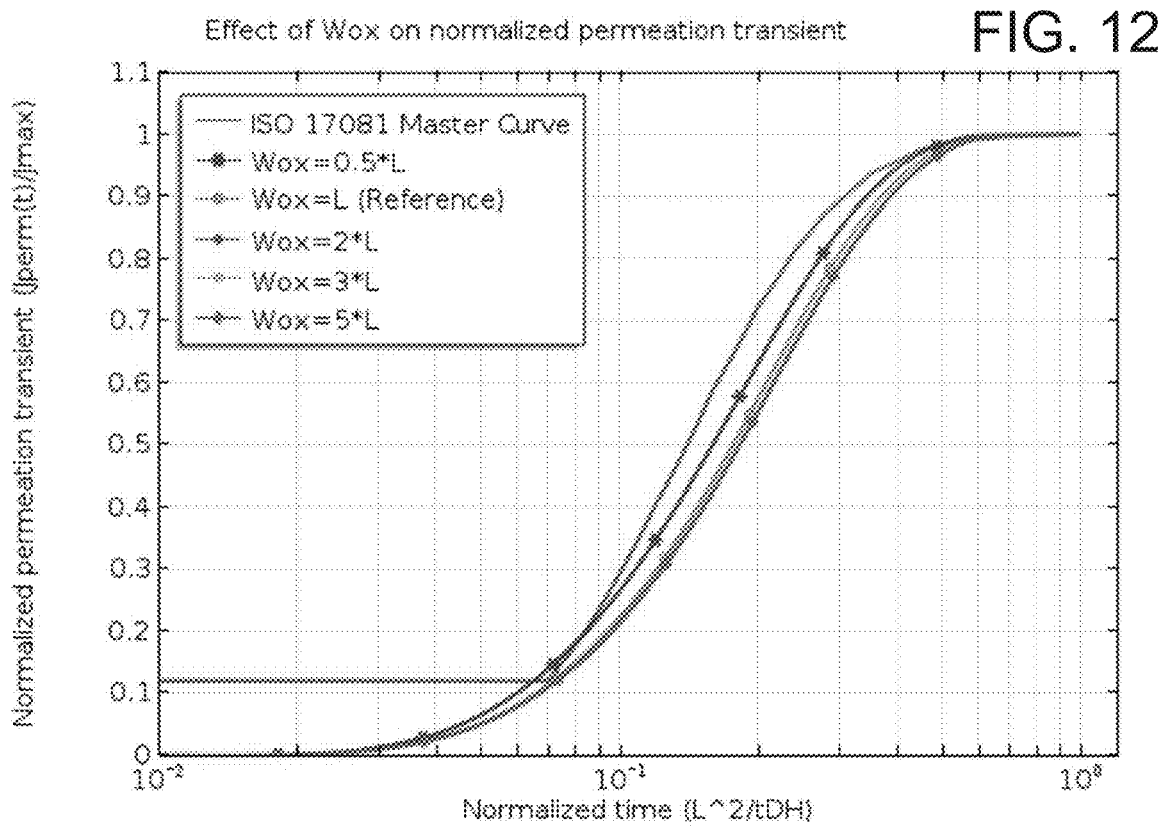

FIG. 12 shows results of a simulation of hydrogen flux for the apparatus of FIGS. 3A, 3B by varying the value $W_{ox}$ and keeping other parameters constant according to the simulated master graphs technique of the present invention.

Figure 13:
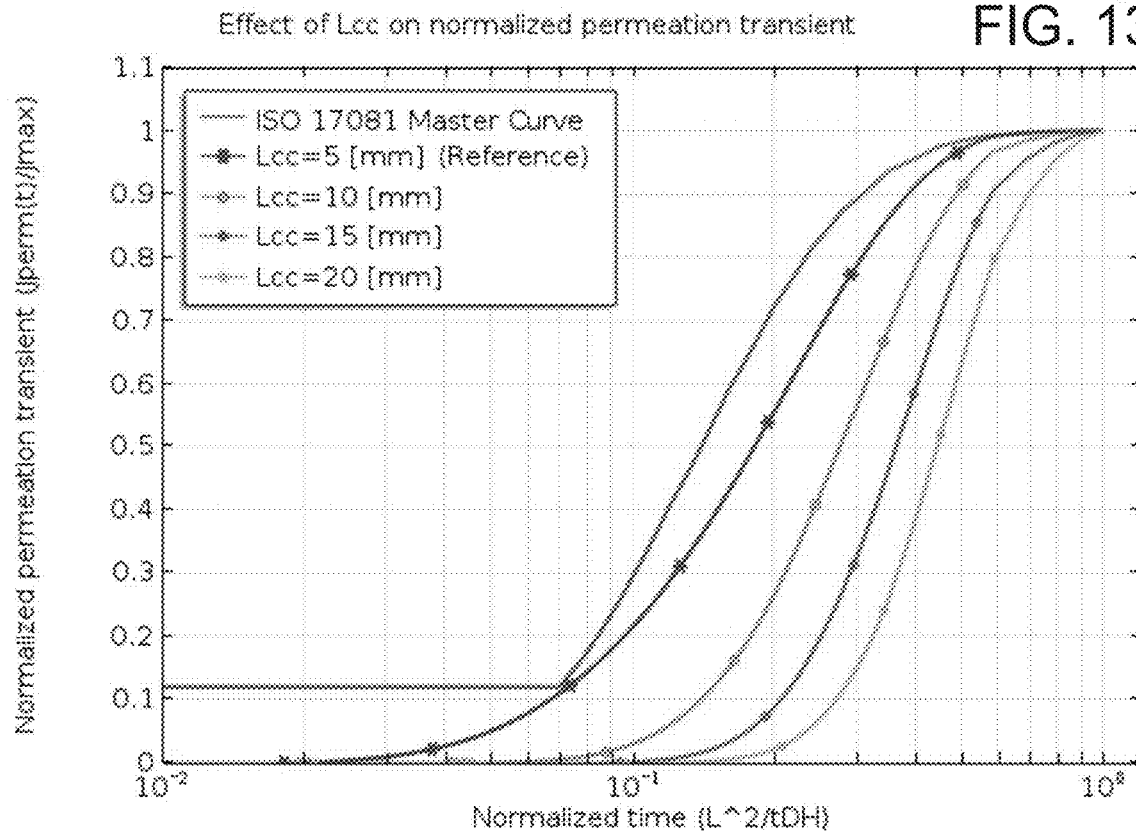

FIG. 13 shows results of a simulation of hydrogen flux for the apparatus of FIGS. 3A, 3B by varying the value $L_{cc}$ and keeping other parameters constant and keeping other parameters constant according to the simulated master graphs technique of the present invention.

Figure 14:
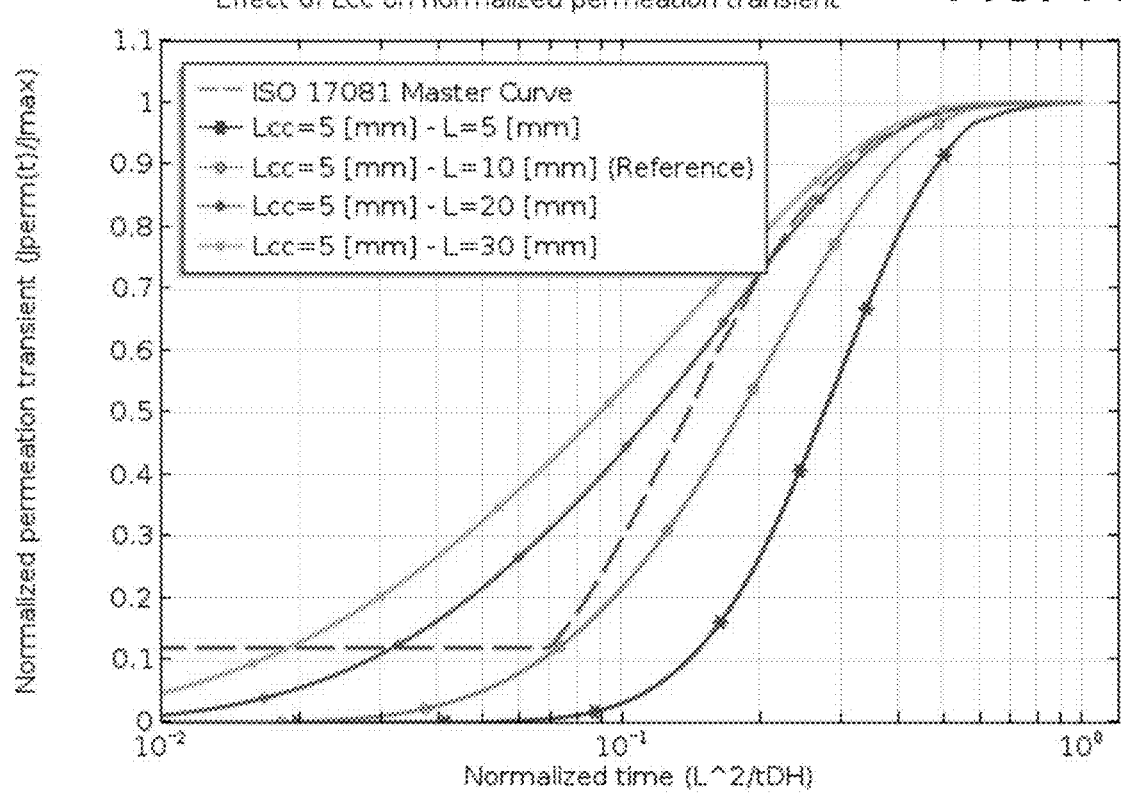

FIG. 14 shows results of a simulation of hydrogen flux for the apparatus of FIGS. 3A, 3B by varying the value L and keeping other parameters constant and keeping other parameters constant according to the simulated master graphs technique of the present invention.

Figure 15:
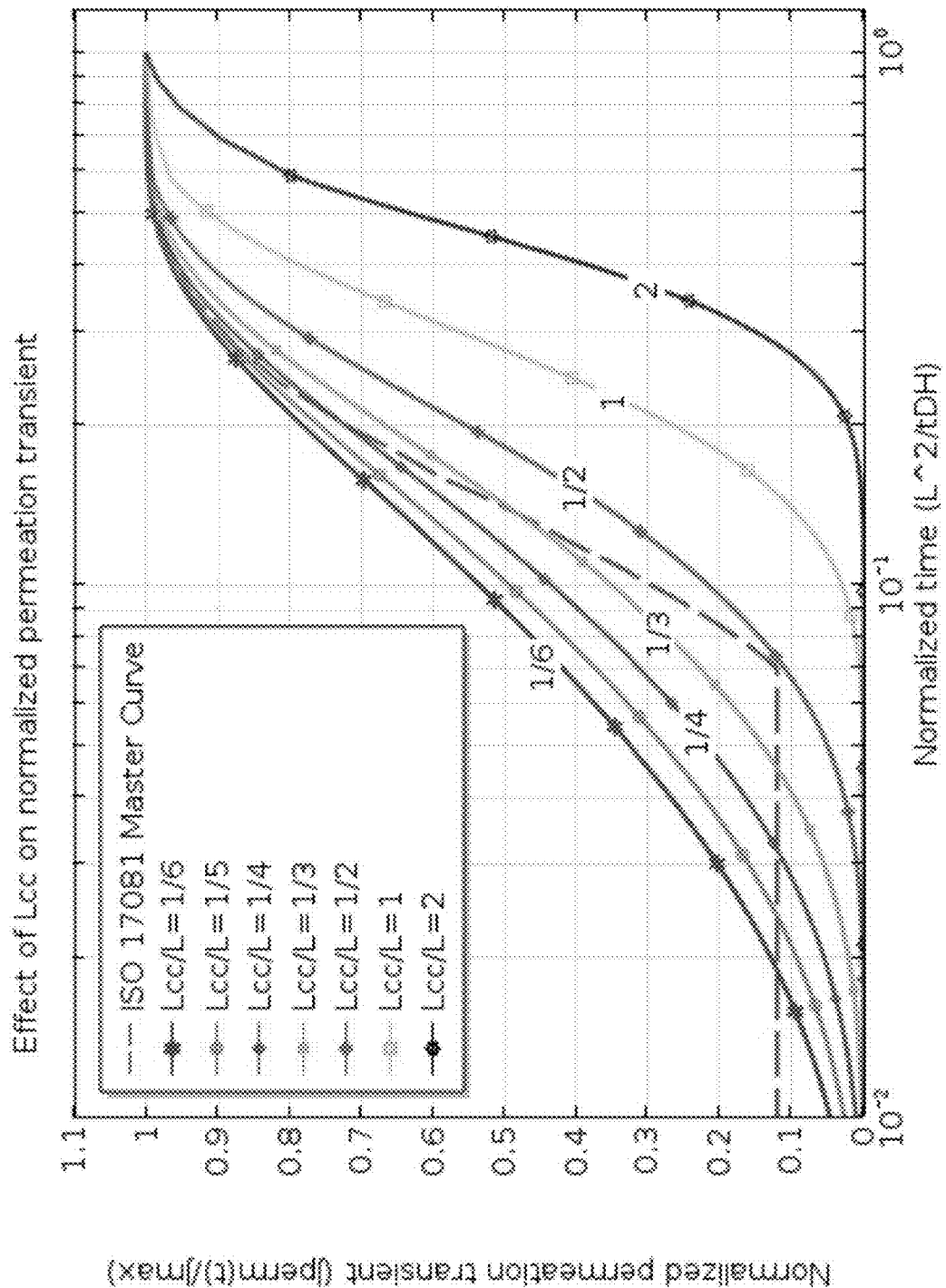

FIG. 15 shows a graph including a set of master curves for the apparatus of FIGS. 3A, 3B be generated for different values of $L_{cc}/L$ according to the simulated master graphs technique of the present invention.

DETAILED DESCRIPTION

By way of overview, embodiments of the present invention use part of the external surface of a metal structure to be investigated as a hydrogen charging surface, and an adjacent part of the external surface as an oxidation surface. Hydrogen atoms are generated at the charging surface, enter the metal, and then a portion of the generated hydrogen atoms diffuse toward the oxidation surface in a three-dimensional stream pattern. By measuring the transient flux over time of the total hydrogen collected at or near the oxidation surface, the hydrogen diffusion coefficient $D_H$ can be determined using embodiments of a simulation method adapted for two or three-dimensional hydrogen flux.

When hydrogen penetrates the metal at the charging surface, it tends to diffuse to low chemical potential (i.e., low hydrogen concentration) areas at a speed that is proportional to the gradient of hydrogen concentration. In other words, hydrogen tends to leave the metal by taking the "shortest chemical path". In metallic structures used in industry having wall thicknesses higher than a millimeter, the shortest chemical path is not necessarily through the thickness of wall from the outer surface to the inner surface. Instead, complex three-dimensional diffusion patterns occur. FIG. 2A is a schematic cross-sectional illustration of a wall of a metal structure 205, permeated by a hydrogen flux according to the present invention via a charging surface 210 and oxidation surface 215. Hydrogen flux lines, e.g., 220 are shown which illustrate semi-circular paths hydrogen atoms follow as they emanate from the charging surface 210 into the metal 205 and then diffuse laterally and upwardly toward the oxidation surface 215. Embodiments of the present invention utilize these flux patterns to extract and measure the residual hydrogen leaving the metal structure 205 from the external wall near the charging surface 210. Since this residual hydrogen diffuses in the metallic structure at a hydrogen diffusivity $D_H$ that is characteristic (i.e., a property) of the metallic material (with proper surface preparation, surface effects are negligible), the time that elapses from the start of the hydrogen flux up to the time that the flux reaches a steady state level at the oxidation surface 215, referred to as the "transient," is correlated with and can be used to determine the $D_H$ of the metal.

FIG. 2B shows an exemplary graph of a charging current over time applied at charging surface 210; FIG. 2C shows an exemplary graph of oxidation current over time measured for three different metallic materials. The current shown in FIG. 2B jumps from zero immediately to a steady current level, while the oxidation currents shown in FIG. 2C ramp up relatively quickly or slowly, depending on the diffusivities of the different metallic materials ($D_{H1}$, $D_{H2}$, $D_{H3}$), up to a steady state level. It is noted that while the steady state levels of oxidation current are the same for all three curves, the curves 232, 234, 236 for the periods in which the oxidation current ramps up from zero up to the steady state level (i.e., the transient curve), are different for each metal. A high diffusivity is associated with a short transient time and a sharp curve, while a low diffusivity is associated with a longer transient time and a slowly rising curve. FIG. 2C therefore illustrates that in order to determine the different hydrogen diffusivities ($D_{H1}$, $D_{H2}$, $D_{H3}$) of the different materials, it is the respective transient curves from which hydrogen diffusivities are derived.

The present invention provides two different groups of apparatuses for obtaining measurements of hydrogen flux transients. In the first group of embodiments, a hydrogen flux probe is placed in proximity to the charging surface for exposure to diverted streams of hydrogen flux. In some embodiments, the hydrogen flux probe measures the flux of hydrogen with a selective detector for $H_2$, e.g. FID. In the second group of embodiments, two electrochemical cells are employed to generate an oxidation current, and the transient of an oxidation current is used a proxy for the hydrogen flux variation. In both sets of embodiments, the hydrogen flux is measured or derived over time to determine the transients of the hydrogen flux prior to reaching steady state level.

Hydrogen Flux Probe Embodiments

FIG. 3A is a top cross-sectional view and FIG. 3B is a side cross-sectional of a first embodiment of an apparatus for non-destructive measurement of $D_H$ according to the principles disclosed herein. Referring to FIG. 3B, which shows the apparatus 300 installed on a surface of a metal to be tested, the apparatus 300 includes an outer casing 305 made of an electrically insulating material that is also chemically resistant to mildly acidic electrolytes (e.g., electrolytes of pH in the range of 3.5 to 4.5). Exemplary materials that meet these qualifications include polymeric compounds such as polypropylene(PP), polyethylene(PE), polymethyl-methacrylate (PMMA), polyvinylidene fluoride (PVDF), polytetrafluoro-ethylene(PFTE), polyimide 11 (PA 11) and polyetheretherketone (PEEK). The outer casing 305 is hollow and can be cylindrical in form, although other configurations are possible. An inner casing 310 of a smaller size than the outer casing 305 is positioned within the first casing. The inner casing 310 is also electrically insulating and can be made of the same or similar materials as the outer casing 305. In some implementations, the inner casing 310 is also hollow and can be cylindrical in form. When installed on the surface of a metal to be tested, it is preferable for the inner casing 310 to be positioned concentrically within the outer casing 305. Outer chamber 315 is defined as the region between the outer casing 305 and the inner casing 310; inner chamber 317 is defined as region in the interior of second casing 310. In some implementations, a first O-ring 307 is set within a groove on the bottom of the outer casing 305.

Similarly, in some implementations a second O-ring 312 is set within a groove on the bottom of the inner casing 310.

During a measurement operation, the outer casing 305 and inner casing 310 are placed and onto the external surface 320 of a metal structure and sealed with respect to the surface by O-rings 307, 312. Once the interface between the bottom of casings 305, 310 and the surface 320 is sealed, the outer chamber 315 is filled substantially (e.g., 70-90 percent of the chamber volume) with an electrolyte solution 325 shown as dashed lines within the outer chamber. The electrolyte 325 thus comes into direct contact with the surface 320 of the metal structure of interest at the bottom of outer chamber 315. The interface between the electrolyte 325 and the metal surface 320 is termed the "charging surface". In this arrangement, the metal surface itself acts as a working electrode. A range of electrolyte solutions can be employed depending on the target level of hydrogen changing and duration of the hydrogen permeation measurement performed. A buffer can be used to maintain constant pH throughout a measurement. Exemplary solutions include 0.1/M sodium hydroxide, 3.5% sodium chloride, and 0.1M sulphuric acid solutions.

A counter electrode 330 is positioned within the electrolyte 325 in the outer chamber 315. In some embodiments, the counter electrode 330 comprises a platinum mesh. In other embodiments, to reduce costs, carbon electrodes or other suitable electrodes that do not react with the electrolyte solution 325 at the applied potential can be used. In some embodiments, a reference electrode 335, used to measure voltage, is also positioned in outer chamber 315. Any suitable commercially available reference electrode can be used, including a Calomel electrode or silver-silver chloride electrode. However, use of a reference electrode in the charging cell is optional and not required. An annular lid 340 conforms to and fits over the outer chamber 315 and couples to the outer casing 305 and inner casing 310. In some implementations, the lid 340 is coupled to the outer and inner casings 305, 310 through one or more O-rings to ensure containment of electrolyte 325. Referring to FIG. 3A, the lid 340 includes holes 342 through which leads can be extended to or from the counter electrode 330 and reference electrode 335.

An electric power supply 345 is coupled at a negative terminal to the metal surface 320, at a positive terminal to a lead of counter electrode 330. In some embodiments, the power supply 345 also includes a neutral terminal to a lead of reference electrode 335. Throughout the present disclosure, it should be understood that the charging apparatus can also be a simple DC with metal at the negative pole and a counter electrode at the positive pole, with no need for a reference electrode, which is optional. The electric power supply 345 preferably runs in galvanostat (i.e., constant current) mode in order to maintain a constant current between the metal surface 320 (working electrode) and the counter electrode 330. The constant current induces electrolysis and generation of hydrogen atoms at the interface between metal surface 320 and electrolyte 325. A fraction of hydrogen atoms evolve as dihydrogen and of this fraction, a certain sub-fraction penetrates into the metal. If the metal surface is of sufficient thickness, e.g., greater than one millimeter, the hydrogen entering the metal surface diffuses in complex flux patterns based on concentration gradients. Some of the hydrogen flux is diverted toward inner chamber 317.

Positioned within the inner chamber 317 is a hydrogen flux sensor 350, such as a hydrogen flux sensor, operative to detected hydrogen flux diverted into the inner chamber 317.

In some embodiments, a commercially available hydrogen flux probe is employed. An example of a suitable hydrogen flux probe is the HYDROSTEEL™ 6000 hydrogen flux monitor instrument manufactured by IonScience of Cambridge, UK. The hydrogen flux sensor is selected to have a sufficient sensitivity to detect approximately 1 pl/cm$^2$/s. A view of an implementation of the apparatus according to FIGS. 3A, 3B specifically including a HYDROSTEEL™ 6000 instrument 391 and accompanying gas conduit 392 is shown in FIG. 3E.

FIGS. 3C and 3D depict a top cross-sectional view and a side cross-sectional view of another embodiment of an apparatus for measuring hydrogen diffusivity having a different geometrical configuration. Apparatus 360 includes a single casing 365 that is divided into first and second chambers 370, 372 by a wall 375. The casing 360 is rectangular in form, as are the first and second chambers 370, 372. In this embodiment, a counter electrode 377 and an optional reference electrode 378 (which can be similar to the first embodiment of FIGS. 3A, 3B) are positioned in the second chamber 372. The second chamber 372 is filled with an electrolyte solution 380. The electrolyte solution 380 directly contacts the surface of metal structure 320. Hydrogen flux sensor 382, including gas outlet port 384 is positioned at the bottom of the first chamber 370 so as to receive hydrogen flux streams diverted toward the first chamber 370. A galvanostat 385 (or alternatively, a simple DC power supply) is coupled to the metal surface 320, counter electrode 377 and reference 378 as in the embodiment of FIGS. 3A and 3B. The galvanostat 385 generates a charging current that induces generation of hydrogen atoms in the electrolyte which then diffuse into the metal surface 320. A lid 387 conforms to and covers the first and second chambers 370, 372, and includes a first opening 388 for the gas outlet port 384 and further openings 389, 390 for passing leads of the counter electrode 377 and reference electrode 378.

In general, the apparatuses of FIG. 3A-3D are adaptable so as to be used with a variety of commercially available hydrogen flux sensors, and the geometrical designs of the chambers can be configured to suit the characteristics of desired hydrogen flux sensors in specific applications. For example, FIG. 3F is a view of an implementation of the apparatus according to FIGS. 3A, 3B that includes an inlet for an ion pump 393 instead of a hydrogen flux sensor. The ion pump (not shown in FIG. 3F) creates a vacuum and the current required to maintain the vacuum gives an indication of the hydrogen flux.

Additional embodiments of an apparatus for measuring hydrogen diffusivity are shown in FIGS. 3G, 3H and 3I. The apparatus shown in FIG. 3G is identical to the apparatus 300 of FIG. 3B except for the addition of a sealing element 396 that is included to ensure the complete sealing of the charging and oxidation cells on the metal surface. The sealing element 396 can be implemented as a magnet (as shown), or for small structures, as a strap to mechanically secure the cell to the apparatus to the structure to be tested. FIG. 3H is a cross-sectional view of another embodiment of the apparatus 397 which is also identical to the apparatus 300 of FIGS. 3A, 3B with the addition of an alignment element used to ensure alignment between the outer casing and inner casing. In the depicted implementation, the alignment element can comprise a hollow annular insert having ribs, e.g., 399 that can prevent relative movement between the inner and outer casings. In another implementation, the alignment element can comprise a groove in the lid (not shown).

In operation, if the metal structure to be tested includes a non-metallic coating, the coating is removed to allow direct contact between at least the charging surface of the apparatus and the metal surface. However, if the interface between metallic surface and coating and the coating itself are hydrogen permeable, the coating does not need to be removed from the oxidation surface portion area on the structure surface. After any such preliminary preparation, the apparatus is first installed on the surface of the metal structure. The electrolyte is then added to the outer chamber. The negative electrode of the electric power supply is connected to the metal structure (working electrode) and the positive electrode to the counter electrode. The reference electrode is connected to the Galvanostat. A constant current is then applied between the counter electrode. The hydrogen flux sensor is used to measure the hydrogen flux as it changes over time (the transient) within the inner chamber. A suitable method is then employed to derive the hydrogen diffusivity of the metal from the measured hydrogen flux transient.

Experiments performed with the apparatus 300 of FIGS. 3A, 3B show that the apparatus is able to detect high hydrogen flux even at low current density. A graph of hydrogen flux over time taken during one such experiment is shown in FIG. 3J. The high yield of detected hydrogen flux makes modeling simpler, and enables use of less sensitive hydrogen flux sensors in the apparatus. As shown in the figure, testing can be performed over an extended period to reach a final steady state current (e.g., about 25-30 hours).

The embodiments of the apparatus that include a hydrogen flux sensor (probe) described above have a number of benefits and advantages. The apparatus can be used to determine the hydrogen diffusion coefficient ($D_H$) of metals equipment in the field, without damage to the equipment. Application of the apparatus requires little surface preparation, and does not require use of expensive palladium foils or coatings. Moreover, embodiments of the apparatus can be combined with other hydrogen flux measurement techniques and existing commercial devices. As noted above, use of platinum for counter electrodes in the charging cell is not compulsory. Alternative electrodes, such as carbon electrodes, can be used so long as they do not react with the electrolyte solution of the charging cell.

Electrochemical Probe Embodiments

FIG. 4A is a top cross-sectional view and FIG. 4B is a side cross-sectional of another embodiment of an apparatus for non-destructive measurement of $D_H$ according to the principles disclosed herein. Referring to FIG. 4B, which shows the apparatus 400 installed on a surface of a metal to be tested, the apparatus 400 includes two electrochemical cells, a charging cell 410 and an oxidation cell 420. Charging cell 410 cell is positioned in an inner chamber 411 enclosed within an inner casing 412. The inner casing is, in turn, positioned within an outer casing 414. An outer chamber 415 is positioned between the inner casing 412 and the outer casing 414. Both the outer casing 414 and inner casing 412 are made of an electrically insulating material that is also chemically resistant to mildly acidic electrolytes (e.g., electrolytes of pH in the range of 3.5 to 4.5). Exemplary materials that meet these qualifications include polymeric compounds such as polypropylene(PP), polyethylene(PE), polymethyl-methacrylate (PMMA), polyvinylidene fluoride (PVDF), polytetrafluoro-ethylene(PFTE), polyimide 11(PA 11) and polyether-etherketone (PEEK). In the embodiment of FIG. 4B, the inner and outer casings 412, 414 are hollow and can be cylindrical in form, although other configurations can be used. When installed on the surface of a metal to be tested, it is preferable for the inner casing 412 to be positioned concentrically within the outer casing 414. Inner chamber 411 contains an electrolyte solution 416 that is in direct contact with the external surface 430 of a metallic structure to be tested. The interface between the electrolyte 416 and the metal surface 430 is termed the "charging surface". A range of electrolyte solutions can be employed depending on the target level of hydrogen changing and duration of the hydrogen permeation measurement performed. A buffer can be used to maintain constant pH throughout a measurement. Exemplary solutions including a 0.1/M sodium hydroxide, 3.5% sodium chloride, and 0.1M sulphuric acid solutions.

A counter electrode 417, which functions as the cathode of the charging cell, and an optional reference electrode 418, used for accurate voltage measurement, are positioned in the electrolyte 416. In some implementations, counter electrode 417 is a platinum mesh similar to those used in standard electrochemical cells. The reference electrode 418 can be implemented as a standard calomel electrode. In order to contain the electrolyte 416 within inner chamber 411, an O-ring 419 is coupled to the bottom of the inner casing 412, and an O-ring 419 is coupled to the bottom of the outer casing 414 by insertion in a groove (not shown). An electric DC power supply 440 operable to provide a constant current is coupled at a negative terminal to metal surface 430, at a positive terminal to counter electrode 417, and, in embodiments in which a reference electrode is employed, at a neutral terminal to reference electrode 418. The power supply 440 generates a potential difference between the metal surface 430 and the counter electrode 417 which induces an ionic current, and also causes a certain amount of hydrolysis of water molecules at the metallic surface. A fraction of hydrogen atoms evolve as dihydrogen and a sub-fraction of this fraction penetrates/diffuses into the metal.

An oxidation cell 420 is positioned in the outer chamber 415 of apparatus 400. Oxidation cell 420 includes a counter electrode 421 and a reference electrode 422 positioned within outer chamber 415. Counter electrode 421 and reference electrode 422 can be implemented using similar materials as those used for counter electrode 417 and reference electrode 418, respectively. The outer chamber 415 is filled with an electrolyte solution 423 which directly contacts metal surface 430 at an "oxidation surface". Electrolyte solution 423 can but does not have to have the same characteristics as the electrolyte 416 of the charging cell 410. In some implementations, a 0.1/1M sodium hydroxide solution can be used for the electrolyte 423, although a wide range of other solutions can be used. In order to contain the electrolyte 423 within outer chamber 415, an O-ring 424 is coupled to the bottom of the outer casing 414. An electric power supply 445 operable to provide a constant voltage (voltage source mode) is coupled at a positive terminal to metal surface 430, at a negative terminal to counter electrode 421, and at a neutral terminal to reference electrode 422 by insertion in a groove (not shown).

A coating 450, which is preferably made of palladium, is deposited on the oxidation surface of the metal that is in contact with the electrolyte 423 of oxidation cell 420. The coating 450 promotes oxidation of hydrogen atoms that reach the oxidation surface. The coating can be prepared in any of the ways know to those of skill in the art. A lid 460 conforms to and fits over both the inner chamber 411 and outer chamber 415. Referring to FIG. 4A, the lid 460 includes a first pair of openings 461, 462 positioned when the lid is in place over the inner chamber 411 to allow electrical leads to couple counter electrode 417, and reference electrode 418, to electric power supply 440. Similarly, lid 460 includes a second pair of openings 463, 464 to allow electrical leads to couple the counter electrode 421 and reference electrode 422 to electric power supply 445.

FIGS. 4C and 4D depict a top cross-sectional view and a side cross-sectional view of another embodiment of an apparatus for measuring hydrogen diffusivity in which the positions of charging cell and the oxidation cell are switched. Referring to FIG. 4D, the apparatus 470 includes two electrochemical cells, an oxidation cell 475 and a charging cell 485. Oxidation cell 475 is positioned in an inner chamber 471 enclosed within an inner casing 472. The inner casing 472 is, in turn, positioned within an outer casing 474. Charging cell 485 is positioned in outer chamber 476 positioned between the inner casing 472 and outer casings 474. Both the inner casing 472 and the outer casing 474 are made of an electrically insulating material that is also chemically resistant to mildly acidic electrolytes such as those described above with regard to the apparatus of FIGS. 4A and 4B.

Inner chamber 475, which comprises the oxidation cell, contains an electrolyte solution 477 that is in direct contact with the external surface 490 of a metallic structure to be tested. In some implementations, a 0.1/M sodium hydroxide solution can be used for the electrolyte 477, although a wide range of other solutions can be used. The bottom of inner casing 472 can include or be coupled to a sealing element such as an O-ring 481 to prevent leaking of the electrolyte 477. The interface between the electrolyte 477 and the metal surface 490 is in this embodiment the oxidation surface. A coating 484, which is preferably made of palladium, is deposited on the oxidation surface of the metal that is in contact with the electrolyte 477 of oxidation cell 475. A counter electrode 478 and a reference electrode 479 are positioned in the electrolyte solution 477. An electric power supply 495 operable as a constant voltage source is coupled at a positive terminal to the metal surface 490, at a negative terminal is coupled to counter electrode 478 and at a neutral terminal is coupled to reference electrode 479. Outer chamber 485, which comprises the charging cell, also includes an electrolyte solution 486 which may be similar to the solution used for the charging cell described above with reference to FIGS. 4A, 4B. The bottom of outer casing 474 can include or be coupled to a sealing element such as an O-ring 482 to prevent leaking of the electrolyte 486. The interface between the electrolyte 486 and the metal surface 490 is in this embodiment is the charging surface. A counter electrode 487 and a reference electrode 488 (optional) are positioned in electrolyte solution 486. An electric power supply 497 operable as a constant current source is coupled at a positive terminal to the metal surface 490, at a negative terminal to counter electrode 487, and, optionally, at a neutral terminal to reference electrode 488. A lid 483 conforms to and fits over both the inner chamber 471 and outer chamber 476 and includes openings (not shown) for electrical leads to the electrodes of the apparatus 470.

It is noted that the electric power supplies 440, 445, 495, 497 in the embodiments depicted are coupled to and controlled by a computing device (not shown) which can modify the respective applied current and voltages to achieve accurate hydrogen detection.

A further embodiment of an apparatus for measuring hydrogen diffusivity according to the present invention is shown in FIGS. 4E and 4F. The apparatus 491 is similar in configuration to the apparatus shown in FIGS. 3C and 3D above (i.e., rectangular and double-chambered), the difference being that the apparatus 491 includes both a charging cell 492 and an oxidation cell 493. Otherwise, the apparatus of FIGS. 4E and 4F are similar to the other electrochemical cell embodiments described with reference to FIGS. 4A-4D. Another embodiment of an apparatus for measuring hydrogen diffusivity 498, shown in FIG. 4G is identical to the apparatus 300 of FIG. 4B except for the addition of a sealing element 499 that is included to ensure the complete sealing of the charging and oxidation cells on the metal surface. The sealing element 499 can be implemented as a magnet, or for small structures, as a strap to mechanically secure the cell to the apparatus to the structure to be tested.

In operation, if the metal structure to be tested includes a non-metallic coating, the coating is removed. After such preliminary preparation, the apparatus is first installed on the surface of the metal structure. Electrolyte is then added to the oxidation cell. The voltage between the oxidation surface of the working electrode and the reference electrode of the oxidation cell is then set using the electric power supply configured in constant voltage mode at approximately +300 mV. Once the oxidation current $I_{ox}$ in the oxidation cell has stabilized, electrolyte is added to the charging cell. A constant charging current is then set using the electric power supply configured in Galvanostat mode. Once the charging current has started, the transient of the oxidation current ($I_{ox}$) at the oxidation cell, which is representative of the hydrogen flux, is monitored until a steady state is reached. A suitable method is then employed to derive the hydrogen diffusivity of the metal from transient of the oxidation current.

Methods of Determining Hydrogen Diffusivity

Since the standard time lag method developed under a one-dimensional diffusion approximation cannot be used for determine $D_H$ for the multi-dimensional hydrogen streams, the present invention provides both a 1) direct simulation method and 2) a simulated master graph method to determine $D_H$.

Direct Simulation Method

In the direct simulation method, an optimization problem in which the hydrogen diffusion kinetics approximated by a Fickian diffusion model with apparent diffusivity $D_H$ is solved at each optimization step (for example using finite element) with a different value of $D_H$(incremental approach). In other words, the direct simulation method simulates and best fits the field results for every single field measurement (or also called the inverse problem). The direct simulation method can employ finite element analysis technique in this method. This iterative simulation is stopped, and the optimum $D_H$ is reached, when the best fit between the numerically simulated permeation curve and the experimentally measured one is obtained.

The diffusion model to be solved at each iteration is given in Eq. 4. A set of boundary conditions and initial conditions, which depend on the apparatus design and service conditions, are associated to Eq. 4.

$$\frac{\partial C}{\partial t} = D_H \Delta^2 C = D_H \left( \frac{\partial^2 C}{\partial x^2} + \frac{\partial^2 C}{\partial y^2} + \frac{\partial^2 C}{\partial z^2} \right) \quad (4)$$

The boundary conditions associated with, for example, the apparatus 300 of FIGS. 3A, 3B design are shown in FIG. 5. The boundary conditions include the hydrogen charging concentration ($C_0$), the thickness of the metal tested (L), the wall thickness of the charging cell ($L_{cc}$), the radius of the charging surface ($R_{ch}$) (more generally, the size of the charging surface), and the width of the oxidation surface ($W_{ox}$). A typical solution of the above boundary value problem is illustrated in FIG. 6, which illustrates a distribution of hydrogen concentration C and the streamlines of hydrogen flux throughout the specimen thickness.

In this optimization, the boundary value for the hydrogen charging concentration ($C_0$) provided by the charging cell is arbitrary, and does not influence the value of the normalized steady-state permeation flux at the oxidation surface. This is illustrated by comparison of FIG. 7A with FIG. 7B. FIG. 7A is a graph of hydrogen flux (permeation) over time for several different values of $C_0$. As shown, the steady state permeation is different for the various values of $C_0$. FIG. 7B is a graph of the normalized hydrogen flux over time for the same values of $C_0$. As can be discerned, FIG. 7B shows a single curve, indicating that the normalized flux converges to the same values for all of the values of $C_0$. In other words, the optimization problem shall be carried out considering the normalized flux rather than the actual flux.

Simulated Master Graphs Method

In the simulated master graphs method, a series of "master curves" are generated for a particular apparatus design. The master curves can then be used to determine the value of $D_H$ from the measured permeation transients. Once developed for a given apparatus design, the master graphs become characteristic of the specific design. In this section, a set of master curves are derived from the apparatus design of FIGS. 4A, 4B. However, the same methodology can be applied for other apparatus designs as well, and none of the following description should be taken as limiting the method to a specific design.

By definition, a master curve is independent of the geometrical dimensions of the apparatus concerned, as well as the thickness of the tested metal surface, the value of the metal's hydrogen diffusivity, and the hydrogen charging concentration. To obtain master curves that are independent of these parameters, the following procedure is carried out. First, all of the parameters that have an influence on the measured permeation transient $J_{perm}(t)$ are listed. A sensitivity analysis is then carried out on each parameter by varying one parameter at a time to determine the influence of each parameter on a plot of $$\left(\frac{J_{perm}}{J_\infty}\right) \text{ vs. } \left(\tau = \frac{DH}{tL^2}\right).$$

If the plot (termed the "normalized permeation transient (NPT) plot") remains invariant while the parameter is varied, then the plot is considered to be a master curve. If the plot does not remain invariant, then the parameter of the x-axis is changed, and, if needed, restrictions on the variability of the test parameters are introduced. This procedure is described in greater detail below.

FIG. 8 is a flow chart of an embodiment of a method 800 for determining hydrogen diffusivity using standard master graphs according to the present invention. This flow chart is tailored to the apparatus described in FIGS. 4A and 4B, and in general the specific parameters tested can vary depending on the apparatus design employed including its physical parameters. In a first step 810, parameters that can influence the permeation transient are listed. The parameters can include, for this embodiment, the radius of the hydrogen charging surface ($R_{ch}$), the width of the oxidation surface ($W_{ox}$), the thickness of the metal tested ("specimen") (L) and the wall thickness of the charging cell ($L_{cc}$). In a following step 820, each parameter is fixed to a reference value. A table of exemplary reference values is given in Table 2 below.

TABLE 2

| Parameter | Reference Value | Variation Range | Unit |
|---|---|---|---|
| L | 10 | [5-30] | Mm |
| $R_{ch}$ | L | [0.5 L-5 L] | Mm |
| $W_{ox}$ | L | [0.5 L-5 L] | Mm |
| $L_{cc}$ | L/2 | [0.5 L-2 L] | Mm |

In step 840, the value of $R_{ch}$ (radius of the charging surface) is varied over different values within a variation range, while keeping all other parameters constant. At each variation increment, in step 842, a parametric simulation is performed based on the $R_{ch}$ value. Results of experimental simulations by varying $R_{ch}$ are shown in FIG. 11. With respect to this variable, when the value of $R_{ch}$ is increased to or above the specimen thickness (i.e., $R_{ch} \geq L$), the NPT plot becomes invariant to further increases in $R_{ch}$. Accordingly, the NPT can be considered a master curve provided that $R_{ch} \geq L$.

In step 844, the value of $W_{ox}$ (width of the oxidation surface) is varied over different values within a variation range, while keeping all other parameters constant. At each variation increment, in step 846, a parametric simulation is performed based on the $W_{ox}$ value. Results of experimental simulations by varying $W_{ox}$ are shown in FIG. 12. Like the $R_{ch}$ parameter, when $W_{ox}$ is increased to or above the specimen thickness ($W_{ox} \geq L$), the NPT plot becomes invariant to further increases in $W_{ox}$. Accordingly, the NPT can be considered a master curve provided that $W_{ox} \geq L$.

In step 848, the value of $L_{cc}$ (wall thickness of the charging cell) is varied over different values within a variation range, while keeping all other parameters constant. At each variation increment, in step 850, a parametric simulation is performed based on the $L_{cc}$ value. Results of experimental simulations by varying $L_{cc}$ are shown in FIG. 13. As indicated in FIG. 13, the NPT plot shows a clear dependence on the value of $L_{cc}$ (i.e., it is not invariant with respect to $L_{cc}$). This dependence can be explained by the fact that the width of the charging cell has a substantial effect on the shortest path that hydrogen can travel to reach the oxidation surface.

Similarly, in step 852, the value of L (thickness of the metal specimen) is varied over different values within a variation range, while keeping all other parameters constant. At each variation increment, in step 854, a parametric simulation is performed based on the L value. Results of experimental simulations by varying $L_{cc}$ are shown in FIG. 14. FIG. 14 indicates that the NPT is also not invariant with respect to L, which also affects the shortest path for hydrogen diffusion.

By employing a ratio of $L_{cc}$ to L (i.e., $L_{cc}/L$), the two variables which affect the NPT plots can be converted into a single controlling parameter for the position of the master curve. Provided that the conditions, $R_{ch}$, $W_{ox} \geq L$, a set of master curves can be generated for different values of $L_{cc}/L$. For the apparatus 400 of FIGS. 4A, 4B, a set of hydrogen permeation master curves are shown in FIG. 15. Tabulated values of the curves are presented in Table 3.

TABLE 3

| τ | \multicolumn{7}{c}{$L_{cc}/L$} |
|---|---|---|---|---|---|---|---|
|  | 1/6 | 1/5 | 1/4 | 1/3 | 1/2 | 1 | 2 |
| 0.01 | 0.05 | 0.03 | 0.01 | 0 | 0 | 0 | 0 |
| 0.02 | 0.13 | 0.09 | 0.05 | 0.02 | 0 | 0 | 0 |
| 0.03 | 0.20 | 0.16 | 0.11 | 0.06 | 0.01 | 0 | 0 |
| 0.04 | 0.27 | 0.22 | 0.16 | 0.10 | 0.03 | 0 | 0 |
| 0.05 | 0.32 | 0.28 | 0.22 | 0.14 | 0.05 | 0 | 0 |
| 0.06 | 0.37 | 0.33 | 0.27 | 0.18 | 0.08 | 0 | 0 |
| 0.07 | 0.42 | 0.37 | 0.31 | 0.23 | 0.11 | 0.01 | 0 |
| 0.08 | 0.46 | 0.42 | 0.36 | 0.27 | 0.14 | 0.01 | 0 |
| 0.09 | 0.50 | 0.46 | 0.40 | 0.31 | 0.18 | 0.02 | 0 |
| 0.10 | 0.54 | 0.49 | 0.43 | 0.35 | 0.21 | 0.03 | 0 |
| 0.15 | 0.68 | 0.65 | 0.60 | 0.53 | 0.39 | 0.12 | 0 |
| 0.20 | 0.78 | 0.76 | 0.72 | 0.67 | 0.55 | 0.26 | 0.02 |
| 0.25 | 0.86 | 0.84 | 0.81 | 0.77 | 0.69 | 0.42 | 0.07 |
| 0.30 | 0.91 | 0.90 | 0.88 | 0.85 | 0.79 | 0.56 | 0.15 |
| 0.40 | 0.97 | 0.96 | 0.95 | 0.94 | 0.91 | 0.79 | 0.38 |
| 0.50 | 0.99 | 0.99 | 0.99 | 0.98 | 0.97 | 0.91 | 0.63 |
| 0.60 | 1 | 1 | 1 | 0.99 | 0.99 | 0.97 | 0.81 |
| 0.70 | 1 | 1 | 1 | 1 | 1 | 0.99 | 0.90 |
| 0.80 | 1 | 1 | 1 | 1 | 1 | 0.99 | 0.96 |
| 0.90 | 1 | 1 | 1 | 1 | 1 | 1 | 0.99 |
| 1.0 | 1 | 1 | 1 | 1 | 1 | 1 | 1 |

It is noted that in some embodiments, it is possible to substitute a different parameter for the abscissa parameter $$\left(\tau = \frac{D_H}{tL^2}\right)$$

in order to generate a single master curve for all values of Lee. However, it is preferable in many instances to keep the abscissa parameter for the sake of overall consistency with the standard plot of ISO-17081.

Returning to FIG. 8, in step 855 the master curves are assembled for each of the parameters (for those parameters that are invariant, the NPT plot is used as the master curve). In step 860, once the master curves are generated, they can be used to determine the value of $D_H$ using an experimentally measured hydrogen flux transient. While any point on the master curve can be used, it is common to use the point on the curve where $$\frac{J_{perm}}{J_\infty} = 0.63.$$

$D_H$ can then be calculated from $$D_H = \frac{\tau_{lag} L^2}{t_{lag}}$$

where the value $t_{lag}$ is determined from the experimental measurement. The value of $\tau_{lag}$ is determined directly from the master curve corresponding to the experimental value of $L_{cc}/L$. Tabulated values of $\tau_{lag}$ for different master curves (i.e., different values of $L_{cc}/L$) are shown in Table 4. The method then ends in step 870.

TABLE 4

|  | \multicolumn{6}{c}{$L_{cc}/L$} |
|---|---|---|---|---|---|---|
|  | 1/6 | 1/5 | 1/4 | 1/3 | 1/2 | 1 | 2 |
| $\tau_{lag}$ | 0.13 | 0.14 | 0.16 | 0.19 | 0.22 | 0.33 | 0.5 |

The disclosed apparatus and methods provide several advantageous features. Prominently, the disclosed apparatus and methods provide for determination of hydrogen diffusivity of metal equipment while the equipment is in operation, namely when the metallic structure is subjected to internal pressure (hoop stress etc.) and process temperature.

Some of the methods disclosed herein are intended to be implemented using a programmed computer system. The flowchart and block diagrams illustrating such methods can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It is to be understood that any structural and functional details disclosed herein are not to be interpreted as limiting the systems and methods, but rather are provided as a representative embodiment and/or arrangement for teaching one skilled in the art one or more ways to implement the methods.

It should be understood that although much of the foregoing description has been directed to systems and methods for implanting photonic materials, methods disclosed herein can be similarly deployed other 'smart' structures in scenarios, situations, and settings beyond the referenced scenarios. It should be further understood that any such implementation and/or deployment is within the scope of the system and methods described herein.

It is to be further understood that like numerals in the drawings represent like elements through the several figures, and that not all components and/or steps described and illustrated with reference to the figures are required for all embodiments or arrangements The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing, and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for measuring a hydrogen diffusivity of a metal structure comprising:

a first chamber positioned on an external surface of the metal structure, the first chamber including a hydrogen flux sensor; and a second chamber separated by a wall from and adjacent to the first chamber and positioned on the external surface of the metal structure, the second chamber including a hydrogen charging cell for generating hydrogen and inducing a hydrogen flux into the external surface of the metal structure;

wherein a portion of the hydrogen flux is diverted backwardly and laterally out of the metal surface underlying the first chamber, where the hydrogen flux is measurable by the hydrogen flux sensor.

2. The apparatus of claim 1, wherein the second chamber includes an electrolyte solution in contact with the external surface of the metal structure.

3. The apparatus of claim 2, further comprising a counter electrode and reference electrode position in the electrolyte solution.

4. The apparatus of claim 3, further comprising an electric power supply coupled to the external surface of the metal structure, the counter electrode and the reference electrode, the power supply being operative to provide a constant current between the counter electrode and the external surface of the metal structure to provide cathodic polarization of the metal surface.

* * * * *